US012624095B2

(12) United States Patent (10) Patent No.: US 12,624,095 B2
Gibbons et al. (45) Date of Patent: May 12, 2026

(54) MONOCLONAL ANTIBODIES AGAINST PATHOLOGICAL TAU, AND METHODS OF DETECTION THEREOF

(71) Applicant: THE TRUSTEES OF THE UNIVERSITY OF PENNSYLVANIA, Philadelphia, PA (US)

(72) Inventors: Garrett S. Gibbons, Philadelphia, PA (US); Dawn M. Riddle, Philadelphia, PA (US); John Q. Trojanowski, Philadelphia, PA (US); Virginia M.Y. Lee, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 661 days.

(21) Appl. No.: 17/999,822

(22) PCT Filed: May 25, 2021

(86) PCT No.: PCT/US2021/034056
§ 371 (c)(1),
(2) Date: Nov. 23, 2022

(87) PCT Pub. No.: WO2021/242757
PCT Pub. Date: Dec. 2, 2021

(65) Prior Publication Data
US 2023/0235034 A1     Jul. 27, 2023

Related U.S. Application Data

(60) Provisional application No. 63/029,977, filed on May 26, 2020.

(51) Int. Cl.
| | |
|---|---|
| *A61K 39/395* | (2006.01) |
| *A61K 38/17* | (2006.01) |
| *A61K 39/00* | (2006.01) |
| *A61K 49/00* | (2006.01) |
| *A61K 49/16* | (2006.01) |
| *A61P 25/28* | (2006.01) |
| *C07K 16/00* | (2006.01) |
| *C07K 16/18* | (2006.01) |
| *C12N 15/85* | (2006.01) |
| *G01N 33/50* | (2006.01) |
| *G01N 33/563* | (2006.01) |
| *G01N 33/58* | (2006.01) |
| *G01N 33/68* | (2006.01) |

(52) U.S. Cl.
CPC .......... *C07K 16/18* (2013.01); *A61K 38/1709* (2013.01); *A61K 39/00* (2013.01); *A61K 39/0007* (2013.01); *A61K 39/395* (2013.01); *A61K 39/3955* (2013.01); *A61K 49/0004* (2013.01); *A61K 49/0058* (2013.01); *A61K 49/16* (2013.01); *A61P 25/28* (2018.01); *C07K 16/00* (2013.01); *C07K 16/005* (2013.01); *C12N 15/85* (2013.01); *G01N 33/5058* (2013.01); *G01N 33/563* (2013.01); *G01N 33/58* (2013.01); *G01N 33/6896* (2013.01); *A61K 2039/505* (2013.01); *C07K 2317/24* (2013.01); *C07K 2317/34* (2013.01); *C07K 2317/515* (2013.01); *C07K 2317/52* (2013.01); *C07K 2317/565* (2013.01); *C07K 2317/569* (2013.01); *C07K 2317/622* (2013.01); *C07K 2317/71* (2013.01); *C07K 2317/76* (2013.01); *G01N 2800/28* (2013.01); *G01N 2800/2821* (2013.01); *G01N 2800/2828* (2013.01)

(58) Field of Classification Search
CPC .......................... C07K 16/18; C07K 2317/34; C07K 2317/16; C07K 2317/565; C07K 2317/24; C07K 2317/56; C07K 2317/55; C07K 2317/51; C07K 2317/515; C07K 14/4711; C07K 14/47; C07K 2317/54; C07K 2317/622; A61K 2039/505; A61K 39/3955; A61K 39/395; A61K 39/00; A61K 39/0007; A61K 47/6843; A61K 39/39533; A61K 49/16; A61P 25/28; A61P 25/16; A61P 25/00
See application file for complete search history.

(56) References Cited

U.S. PATENT DOCUMENTS

| | | | | |
|---|---|---|---|---|
| 8,697,076 | B2 * | 4/2014 | Binder | C07K 16/18 |
| | | | | 514/17.7 |
| 9,957,317 | B2 * | 5/2018 | West | A61P 25/28 |
| 2012/0301473 | A1 * | 11/2012 | Binder | G01N 33/6896 |
| | | | | 424/139.1 |

(Continued)

OTHER PUBLICATIONS

Kontsekova et al., Alzheimer's Res. & Thera., 2014;6:45. Alzres. com/content/t/4/45.*

(Continued)

*Primary Examiner* — Chang-Yu Wang
(74) *Attorney, Agent, or Firm* — Saul Ewing LLP; Kathryn Doyle; Domingos J. Silva

(57) ABSTRACT

The present disclosure provides monoclonal antibodies that selectively bind to pathological tau over native tau. In certain aspects, the antibodies inhibit or minimize propagation of tau aggregates and/or reduce spread of pathological tau in vivo. In other aspects, the disclosure comprises a method of treating, ameliorating, and/or preventing a tauopathy in a subject, comprising administering any one of the antibodies of the disclosure to the subject. In yet other aspects, the disclosure comprises methods of detecting pathological tau using any one of the antibodies of the disclosure.

11 Claims, 12 Drawing Sheets

Specification includes a Sequence Listing.

(56)          References Cited

U.S. PATENT DOCUMENTS

| | | | |
|---|---|---|---|
| 2013/0224191 A1 | 8/2013 | Stull | |
| 2014/0193420 A1 | 7/2014 | Aburatani | |
| 2017/0058024 A1* | 3/2017 | West | A61P 25/28 |
| 2017/0306019 A1 | 10/2017 | Carriere | |
| 2018/0193457 A1 | 7/2018 | Sokurenko | |
| 2018/0371066 A1* | 12/2018 | West | A61P 25/28 |
| 2022/0127346 A1* | 4/2022 | Henley | A61P 25/16 |
| 2024/0192230 A1* | 6/2024 | Walt | G01N 33/6854 |
| 2024/0383972 A1* | 11/2024 | Teng | A61P 25/28 |

OTHER PUBLICATIONS

Novak et al., Front. In Neurosci.2018; doi:10.3389/fnins.2018.
00798.*
MacCallum et al., J. Mol. Biol., 1996; 262: 732-745.*
Pascalis et al., The Journal of Immunology, 2002; 169: 3076-3084.*
Casset et al., BBRC, 2003; 307: 198-205.*
Vajdos et al., J. Mol. Biol. 2002; 320: 415-428.*
Holm et al., Mol. Immunol., 2007; 44: 1075-1084.*
Chen et al., J. Mol. Bio., 1999; 293: 865-881.*

Wu et al., J. Mol. Biol., 1999; 294:151-162.*
Gibbons et al. Mol. Neurodeg., 2020; 15:6. doi.org/10.1186/s13024-
020-00404-5 . . . .*
Gibbons Garrett S, Banks Rachel A, Kim Bumjin, Changolkar
Lakshmi, Riddle Dawn M, Leight Susan N, Irwin David J, Trojanowski
John Q, Lee Virginia M Y, "Detection of Alzheimer Disease
(AD)-Specific Tau Pathology in AD and NonAD Tauopathies by
Immunohistochemistry With Novel Conformation-Selective Tau
Antibodies", Journal of neuropathology and experimental neurol-
ogy, Lippincott Williams and Wilkins., New York, NY., New York,
NY. , (Mar. 1, 2018), vol. 77, No. 3, doi:10.1093/jnen/nly010, ISSN
0022-3069, pp. 216-228, XP055879716.
Gibbons Garrett S., Kim Soo-Jung, Wu Qihui, Riddle Dawn M.,
Leight Susan N., Changolkar Lakshmi, Xu Hong, Meymand Emily
S., O'reilly Mia, Zhang Bin, Brunden Kurt R., Trojanowski John Q.,
Lee Virginia M. Y., "Conformation-selective tau monoclonal anti-
bodies inhibit tau pathology in primary neurons and a mouse model
of Alzheimer's disease", Molecular Neurodegeneration, (Nov. 4,
2020), vol. 15, No. 64, doi:10.1186/s13024-020-00404-5, pp. 1-19,
XP055879723.
International Search Report and Written Opinion issued in PCT/
US21/34056, dated Oct. 22, 2021, pp. 1-9.

* cited by examiner

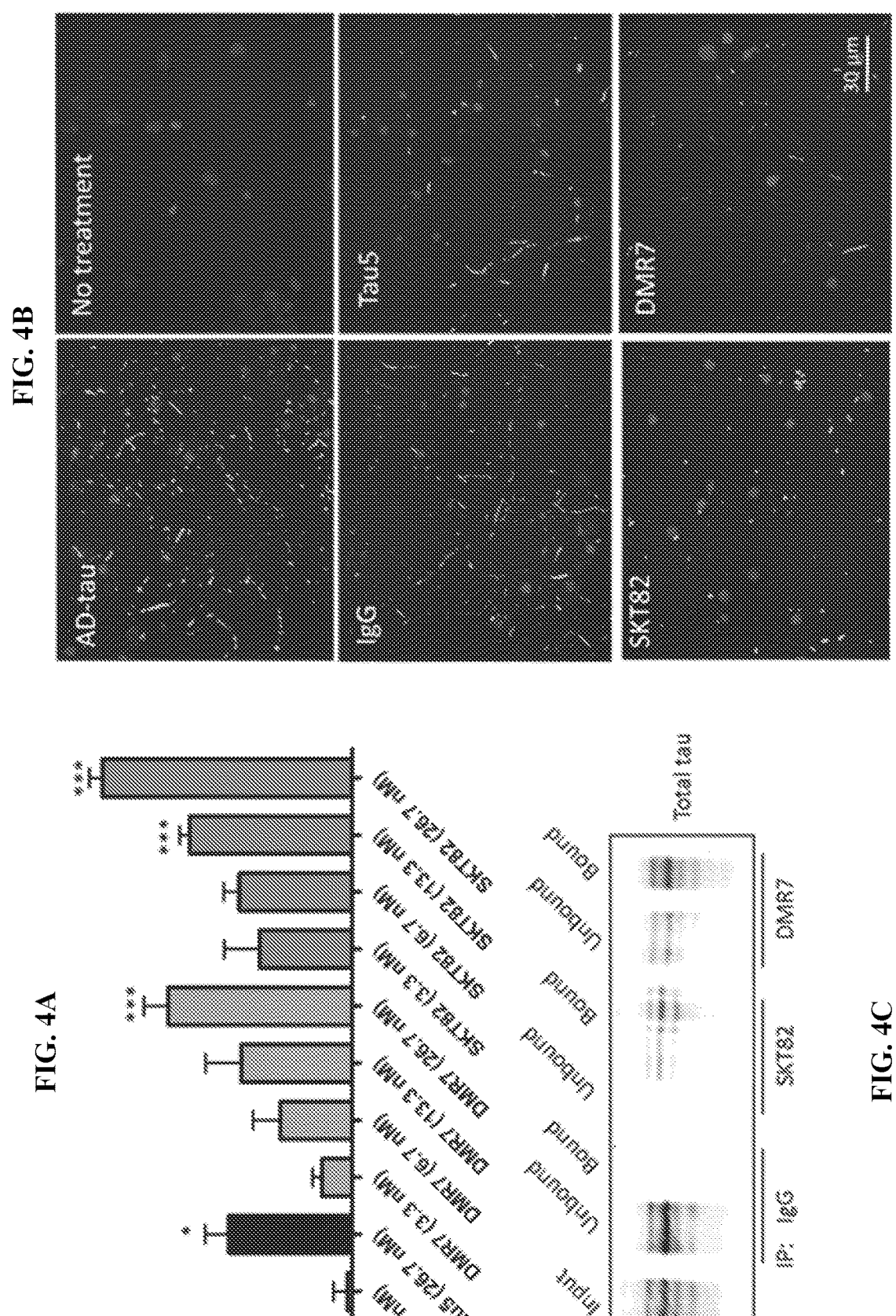

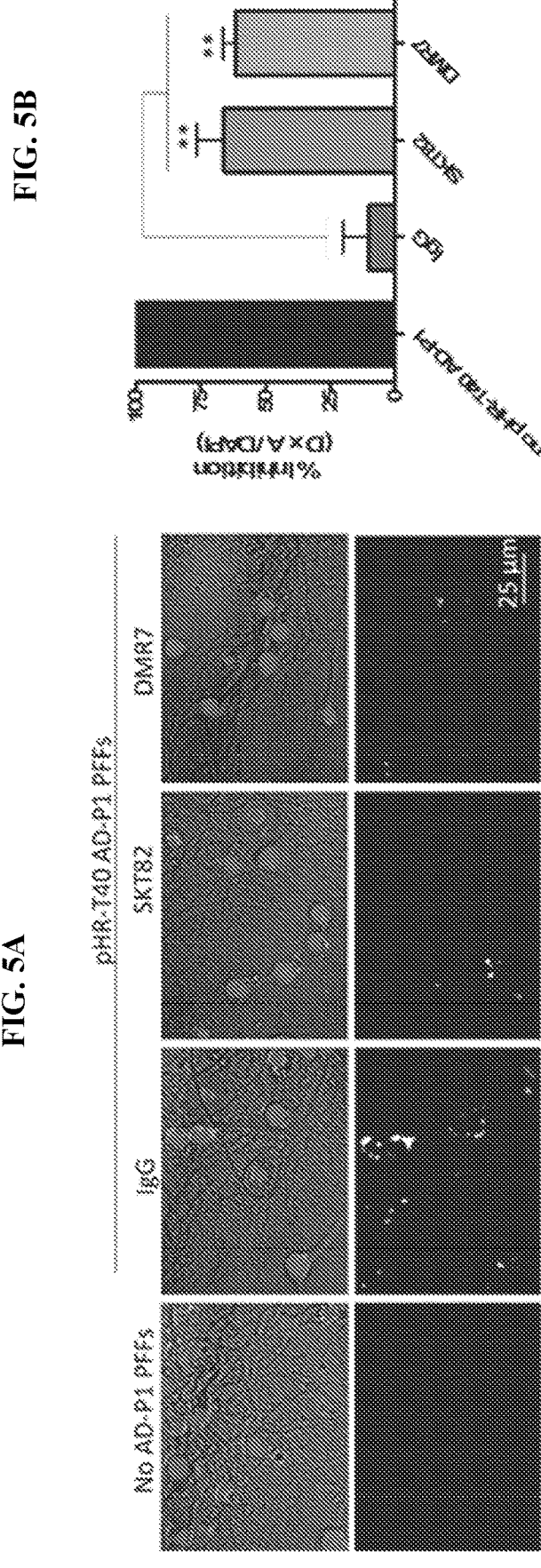

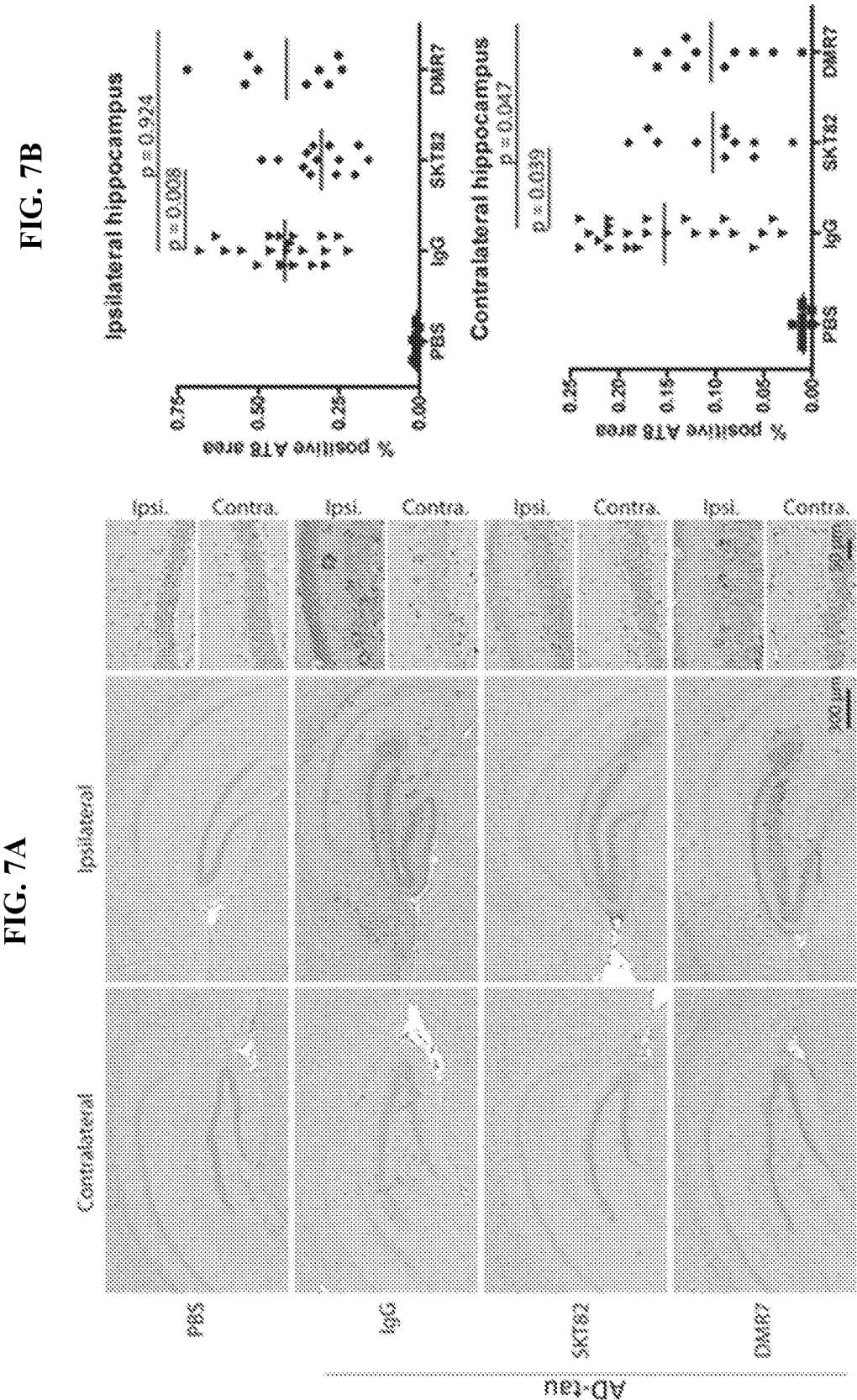

SEQUENCE LISTING

<160> NUMBER OF SEQ ID NOS: 69

<210> SEQ ID NO 1
<211> LENGTH: 90
<212> TYPE: DNA
<213> ORGANISM: Artificial Sequence
<220> FEATURE:
<223> OTHER INFORMATION: Chemically synthesized

<400> SEQUENCE: 1
gaggttcagc tgcagcagtc tggggcagag cttgtgaggt caggggcctc agtcaagttg      60
tcctgcacag cttctggctt caacattaaa                                      90

<210> SEQ ID NO 2
<211> LENGTH: 15
<212> TYPE: DNA
<213> ORGANISM: Artificial Sequence
<220> FEATURE:
<223> OTHER INFORMATION: Chemically synthesized

<400> SEQUENCE: 2
gactactata tgcac                                                      15

<210> SEQ ID NO 3
<211> LENGTH: 42
<212> TYPE: DNA
<213> ORGANISM: Artificial Sequence
<220> FEATURE:
<223> OTHER INFORMATION: Chemically synthesized

<400> SEQUENCE: 3
tgggttaagc agaggcctga acagggcctg gagtggattg ga                        42

<210> SEQ ID NO 4
<211> LENGTH: 51
<212> TYPE: DNA
<213> ORGANISM: Artificial Sequence
<220> FEATURE:
<223> OTHER INFORMATION: Chemically synthesized

<400> SEQUENCE: 4
tggtttgatc ctgagaatgg tgatgctgaa tatgccccga agttccagga c              51

<210> SEQ ID NO 5
<211> LENGTH: 96
<212> TYPE: DNA
<213> ORGANISM: Artificial Sequence
<220> FEATURE:
<223> OTHER INFORMATION: Chemically synthesized

<400> SEQUENCE: 5
aaggccacta tgactgcaga cacatcctcc aacgcagcct acctgcagct cagcagcctg      60
acatctgagg acactgccgt ctattactgt aatggt                               96

<210> SEQ ID NO 6
<211> LENGTH: 9
<212> TYPE: DNA
<213> ORGANISM: Artificial Sequence
<220> FEATURE:
<223> OTHER INFORMATION: Chemically synthesized

<400> SEQUENCE: 6 tatctttac                                                             9

```
<210> SEQ ID NO 7
<211> LENGTH: 33
<212> TYPE: DNA
<213> ORGANISM: Artificial Sequence
<220> FEATURE:
<223> OTHER INFORMATION: Chemically synthesized

<400> SEQUENCE: 7
tggggccaag ggactctggt cactgtctct tca                                     33

<210> SEQ ID NO 8
<211> LENGTH: 30
<212> TYPE: PRT
<213> ORGANISM: Artificial Sequence
<220> FEATURE:
<223> OTHER INFORMATION: Chemically synthesized

<400> SEQUENCE: 8

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys
            20                  25                  30

<210> SEQ ID NO 9
<211> LENGTH: 5
<212> TYPE: PRT
<213> ORGANISM: Artificial Sequence
<220> FEATURE:
<223> OTHER INFORMATION: Chemically synthesized

<400> SEQUENCE: 9

Asp Tyr Tyr Met His
1               5

<210> SEQ ID NO 10
<211> LENGTH: 14
<212> TYPE: PRT
<213> ORGANISM: Artificial Sequence
<220> FEATURE:
<223> OTHER INFORMATION: Chemically synthesized

<400> SEQUENCE: 10

Trp Val Lys Gln Arg Pro Glu Gln Gly Leu Glu Trp Ile Gly
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Chemically synthesized

<400> SEQUENCE: 11

Trp Phe Asp Pro Glu Asn Gly Asp Ala Glu Tyr Ala Pro Lys Phe Gln
1               5                   10                  15

Asp

<210> SEQ ID NO 12
<211> LENGTH: 32
<212> TYPE: PRT
<213> ORGANISM: Artificial Sequence
<220> FEATURE:
<223> OTHER INFORMATION: Chemically synthesized

<400> SEQUENCE: 12

Lys Ala Thr Met Thr Ala Asp Thr Ser Ser Asn Ala Ala Tyr Leu Gln
```

-continued

```
1            5              10              15

Leu Ser Ser Leu Thr Ser Glu Asp Thr Ala Val Tyr Tyr Cys Asn Gly
             20              25              30
```

<210> SEQ ID NO 13
<211> LENGTH: 3
<212> TYPE: PRT
<213> ORGANISM: Artificial Sequence
<220> FEATURE:
<223> OTHER INFORMATION: Chemically synthesized

<400> SEQUENCE: 13

```
Tyr Leu Tyr
1
```

<210> SEQ ID NO 14
<211> LENGTH: 11
<212> TYPE: PRT
<213> ORGANISM: Artificial Sequence
<220> FEATURE:
<223> OTHER INFORMATION: Chemically synthesized

<400> SEQUENCE: 14

```
Trp Gly Gln Gly Thr Leu Val Thr Val Ser Ser
1            5              10
```

<210> SEQ ID NO 15
<211> LENGTH: 69
<212> TYPE: DNA
<213> ORGANISM: Artificial Sequence
<220> FEATURE:
<223> OTHER INFORMATION: Chemically synthesized

<400> SEQUENCE: 15

```
gatgttttga tgacccaaac tccactctcc ctgcctgtca gtcttggaga tcaagcctcc      60
atctcttgc                                                             69
```

<210> SEQ ID NO 16
<211> LENGTH: 48
<212> TYPE: DNA
<213> ORGANISM: Artificial Sequence
<220> FEATURE:
<223> OTHER INFORMATION: Chemically synthesized

<400> SEQUENCE: 16

```
agatctagtc agaacattgt acataataat ggaaacacct atttagaa                   48
```

<210> SEQ ID NO 17
<211> LENGTH: 45
<212> TYPE: DNA
<213> ORGANISM: Artificial Sequence
<220> FEATURE:
<223> OTHER INFORMATION: Chemically synthesized

<400> SEQUENCE: 17

```
tggtaccttc agaaaccagg ccagtctcca aagctcctga tctac                      45
```

<210> SEQ ID NO 18
<211> LENGTH: 21
<212> TYPE: DNA
<213> ORGANISM: Artificial Sequence
<220> FEATURE:
<223> OTHER INFORMATION: Chemically synthesized

<400> SEQUENCE: 18
aaagtttcca accgattttc t 21

<210> SEQ ID NO 19
<211> LENGTH: 96
<212> TYPE: DNA
<213> ORGANISM: Artificial Sequence
<220> FEATURE:
<223> OTHER INFORMATION: Chemically synthesized

<400> SEQUENCE: 19
ggggtcccag acaggttcag tggcagtgga tcagggacag atttcacact caagatcagc 60
agagtggagg ctgaggatct gggaatttat tactgc 96

<210> SEQ ID NO 20
<211> LENGTH: 27
<212> TYPE: DNA
<213> ORGANISM: Artificial Sequence
<220> FEATURE:
<223> OTHER INFORMATION: Chemically synthesized

<400> SEQUENCE: 20
tttcaaggtt cacatgttcc gcacacg 27

<210> SEQ ID NO 21
<211> LENGTH: 30
<212> TYPE: DNA
<213> ORGANISM: Artificial Sequence
<220> FEATURE:
<223> OTHER INFORMATION: Chemically synthesized

<400> SEQUENCE: 21
ttcggagggg ggaccaggct ggaaataaaa 30

<210> SEQ ID NO 22
<211> LENGTH: 23
<212> TYPE: PRT
<213> ORGANISM: Artificial Sequence
<220> FEATURE:
<223> OTHER INFORMATION: Chemically synthesized

<400> SEQUENCE: 22

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 23
<211> LENGTH: 16
<212> TYPE: PRT
<213> ORGANISM: Artificial Sequence
<220> FEATURE:
<223> OTHER INFORMATION: Chemically synthesized

<400> SEQUENCE: 23

Arg Ser Ser Gln Asn Ile Val His Asn Asn Gly Asn Thr Tyr Leu Glu
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Chemically synthesized

<400> SEQUENCE: 24

```
Trp Tyr Leu Gln Lys Pro Gly Gln Ser Pro Lys Leu Leu Ile Tyr
1               5                   10                  15
```

<210> SEQ ID NO 25
<211> LENGTH: 7
<212> TYPE: PRT
<213> ORGANISM: Artificial Sequence
<220> FEATURE:
<223> OTHER INFORMATION: Chemically synthesized

<400> SEQUENCE: 25

```
Lys Val Ser Asn Arg Phe Ser
1               5
```

<210> SEQ ID NO 26
<211> LENGTH: 32
<212> TYPE: PRT
<213> ORGANISM: Artificial Sequence
<220> FEATURE:
<223> OTHER INFORMATION: Chemically synthesized

<400> SEQUENCE: 26

```
Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Ile Tyr Tyr Cys
            20                  25                  30
```

<210> SEQ ID NO 27
<211> LENGTH: 9
<212> TYPE: PRT
<213> ORGANISM: Artificial Sequence
<220> FEATURE:
<223> OTHER INFORMATION: Chemically synthesized

<400> SEQUENCE: 27

```
Phe Gln Gly Ser His Val Pro His Thr
1               5
```

<210> SEQ ID NO 28
<211> LENGTH: 10
<212> TYPE: PRT
<213> ORGANISM: Artificial Sequence
<220> FEATURE:
<223> OTHER INFORMATION: Chemically synthesized

<400> SEQUENCE: 28

```
Phe Gly Gly Gly Thr Arg Leu Glu Ile Lys
1               5                   10
```

<210> SEQ ID NO 29
<211> LENGTH: 75
<212> TYPE: DNA
<213> ORGANISM: Artificial Sequence
<220> FEATURE:
<223> OTHER INFORMATION: Chemically synthesized

<400> SEQUENCE: 29

```
caggtccaac tgcagcagcc tggggctgag ctggtgaggc ctggggcttc agtgaaactg      60
tcctgcaagg cttct                                                       75
```

<210> SEQ ID NO 30
<211> LENGTH: 24
<212> TYPE: DNA
<213> ORGANISM: Artificial Sequence
<220> FEATURE:
<223> OTHER INFORMATION: Chemically synthesized

<400> SEQUENCE: 30
ggctacatct tcaccaccta ctgg                                              24

<210> SEQ ID NO 31
<211> LENGTH: 51
<212> TYPE: DNA
<213> ORGANISM: Artificial Sequence
<220> FEATURE:
<223> OTHER INFORMATION: Chemically synthesized

<400> SEQUENCE: 31
atgaactggg tgaagcagag gcctggacag ggccttgaat ggattgctat g               51

<210> SEQ ID NO 32
<211> LENGTH: 24
<212> TYPE: DNA
<213> ORGANISM: Artificial Sequence
<220> FEATURE:
<223> OTHER INFORMATION: Chemically synthesized

<400> SEQUENCE: 32
attgatcctt cagacagtga aact                                             24

<210> SEQ ID NO 33
<211> LENGTH: 111
<212> TYPE: DNA
<213> ORGANISM: Artificial Sequence
<220> FEATURE:
<223> OTHER INFORMATION: Chemically synthesized

<400> SEQUENCE: 33
cactacaatc aaatgttcaa ggacaaggcc acattgactg tagacacatc ctccagcacg      60
gcctacatgc agctcagcgg cctgacatct gaagactctg cggtctatta c              111

<210> SEQ ID NO 34
<211> LENGTH: 24
<212> TYPE: DNA
<213> ORGANISM: Artificial Sequence
<220> FEATURE:
<223> OTHER INFORMATION: Chemically synthesized

<400> SEQUENCE: 34
tgtgcaagag gggaaggcta ctgg                                             24

<210> SEQ ID NO 35
<211> LENGTH: 30
<212> TYPE: DNA
<213> ORGANISM: Artificial Sequence
<220> FEATURE:
<223> OTHER INFORMATION: Chemically synthesized

<400> SEQUENCE: 35
ggccaaggca ccactctcac agtctcctca                                       30

<210> SEQ ID NO 36
<211> LENGTH: 25
<212> TYPE: PRT
<213> ORGANISM: Artificial Sequence
<220> FEATURE:
<223> OTHER INFORMATION: Chemically synthesized

<400> SEQUENCE: 36

Gln Val Gln Leu Gln Gln Pro Gly Ala Glu Leu Val Arg Pro Gly Ala
1               5                   10                  15

```
Ser Val Lys Leu Ser Cys Lys Ala Ser
            20              25

<210> SEQ ID NO 37
<211> LENGTH: 8
<212> TYPE: PRT
<213> ORGANISM: Artificial Sequence
<220> FEATURE:
<223> OTHER INFORMATION: Chemically synthesized

<400> SEQUENCE: 37

Gly Tyr Ile Phe Thr Thr Tyr Trp
1               5

<210> SEQ ID NO 38
<211> LENGTH: 17
<212> TYPE: PRT
<213> ORGANISM: Artificial Sequence
<220> FEATURE:
<223> OTHER INFORMATION: Chemically synthesized

<400> SEQUENCE: 38

Met Asn Trp Val Lys Gln Arg Pro Gly Gln Gly Leu Glu Trp Ile Ala
1               5                   10                  15

Met

<210> SEQ ID NO 39
<211> LENGTH: 8
<212> TYPE: PRT
<213> ORGANISM: Artificial Sequence
<220> FEATURE:
<223> OTHER INFORMATION: Chemically synthesized

<400> SEQUENCE: 39

Ile Asp Pro Ser Asp Ser Glu Thr
1               5

<210> SEQ ID NO 40
<211> LENGTH: 37
<212> TYPE: PRT
<213> ORGANISM: Artificial Sequence
<220> FEATURE:
<223> OTHER INFORMATION: Chemically synthesized

<400> SEQUENCE: 40

His Tyr Asn Gln Met Phe Lys Asp Lys Ala Thr Leu Thr Val Asp Thr
1               5                   10                  15

Ser Ser Ser Thr Ala Tyr Met Gln Leu Ser Gly Leu Thr Ser Glu Asp
            20                  25                  30

Ser Ala Val Tyr Tyr
        35

<210> SEQ ID NO 41
<211> LENGTH: 8
<212> TYPE: PRT
<213> ORGANISM: Artificial Sequence
<220> FEATURE:
<223> OTHER INFORMATION: Chemically synthesized

<400> SEQUENCE: 41

Cys Ala Arg Gly Glu Gly Tyr Trp
1               5

<210> SEQ ID NO 42
```

-continued

```
<211> LENGTH: 10
<212> TYPE: PRT
<213> ORGANISM: Artificial Sequence
<220> FEATURE:
<223> OTHER INFORMATION: Chemically synthesized

<400> SEQUENCE: 42

Gly Gln Gly Thr Thr Leu Thr Val Ser Ser
1               5                   10

<210> SEQ ID NO 43
<211> LENGTH: 78
<212> TYPE: DNA
<213> ORGANISM: Artificial Sequence
<220> FEATURE:
<223> OTHER INFORMATION: Chemically synthesized

<400> SEQUENCE: 43
gatgttgtga tgacccagac tccactcact ttgtcggtta ccattggaca accagcctcc      60
atctcttgca agtcaagt                                                    78

<210> SEQ ID NO 44
<211> LENGTH: 33
<212> TYPE: DNA
<213> ORGANISM: Artificial Sequence
<220> FEATURE:
<223> OTHER INFORMATION: Chemically synthesized

<400> SEQUENCE: 44
cagagcctct tagatagtga tggaaagaca tat                                   33

<210> SEQ ID NO 45
<211> LENGTH: 51
<212> TYPE: DNA
<213> ORGANISM: Artificial Sequence
<220> FEATURE:
<223> OTHER INFORMATION: Chemically synthesized

<400> SEQUENCE: 45
ttgaattggt tgttacagag cccaggccag tctccaaagc gcctaatctt c               51

<210> SEQ ID NO 46
<211> LENGTH: 9
<212> TYPE: DNA
<213> ORGANISM: Artificial Sequence
<220> FEATURE:
<223> OTHER INFORMATION: Chemically synthesized

<400> SEQUENCE: 46 ctggtgtct                                                              9

<210> SEQ ID NO 47
<211> LENGTH: 105
<212> TYPE: DNA
<213> ORGANISM: Artificial Sequence
<220> FEATURE:
<223> OTHER INFORMATION: Chemically synthesized

<400> SEQUENCE: 47
aaactggact ctggagtccc tgacaggttc actggcagtg gatcagggac agatttcaca      60
ctgaaaatca gcagagtgga ggctgaggat ttgggagttt attat                     105

<210> SEQ ID NO 48
<211> LENGTH: 33
<212> TYPE: DNA
```

-continued

```
<213> ORGANISM: Artificial Sequence
<220> FEATURE:
<223> OTHER INFORMATION: Chemically synthesized

<400> SEQUENCE: 48
tgctggcaag gtacacattt tccgtggacg ttc                                  33

<210> SEQ ID NO 49
<211> LENGTH: 27
<212> TYPE: DNA
<213> ORGANISM: Artificial Sequence
<220> FEATURE:
<223> OTHER INFORMATION: Chemically synthesized

<400> SEQUENCE: 49
ggtggaggca ccaagctgga aatcaaa                                         27

<210> SEQ ID NO 50
<211> LENGTH: 26
<212> TYPE: PRT
<213> ORGANISM: Artificial Sequence
<220> FEATURE:
<223> OTHER INFORMATION: Chemically synthesized

<400> SEQUENCE: 50

Asp Val Val Met Thr Gln Thr Pro Leu Thr Leu Ser Val Thr Ile Gly
1               5                   10                  15

Gln Pro Ala Ser Ile Ser Cys Lys Ser Ser
            20                  25

<210> SEQ ID NO 51
<211> LENGTH: 11
<212> TYPE: PRT
<213> ORGANISM: Artificial Sequence
<220> FEATURE:
<223> OTHER INFORMATION: Chemically synthesized

<400> SEQUENCE: 51

Gln Ser Leu Leu Asp Ser Asp Gly Lys Thr Tyr
1               5                   10

<210> SEQ ID NO 52
<211> LENGTH: 17
<212> TYPE: PRT
<213> ORGANISM: Artificial Sequence
<220> FEATURE:
<223> OTHER INFORMATION: Chemically synthesized

<400> SEQUENCE: 52

Leu Asn Trp Leu Leu Gln Ser Pro Gly Gln Ser Pro Lys Arg Leu Ile
1               5                   10                  15

Phe

<210> SEQ ID NO 53
<211> LENGTH: 3
<212> TYPE: PRT
<213> ORGANISM: Artificial Sequence
<220> FEATURE:
<223> OTHER INFORMATION: Chemically synthesized

<400> SEQUENCE: 53

Leu Val Ser
1

<210> SEQ ID NO 54
```

<211> LENGTH: 35
<212> TYPE: PRT
<213> ORGANISM: Artificial Sequence
<220> FEATURE:
<223> OTHER INFORMATION: Chemically synthesized

<400> SEQUENCE: 54

```
Lys Leu Asp Ser Gly Val Pro Asp Arg Phe Thr Gly Ser Gly Ser Gly
1               5                   10                  15

Thr Asp Phe Thr Leu Lys Ile Ser Arg Val Glu Ala Glu Asp Leu Gly
            20                  25                  30

Val Tyr Tyr
        35
```

<210> SEQ ID NO 55
<211> LENGTH: 11
<212> TYPE: PRT
<213> ORGANISM: Artificial Sequence
<220> FEATURE:
<223> OTHER INFORMATION: Chemically synthesized

<400> SEQUENCE: 55

```
Cys Trp Gln Gly Thr His Phe Pro Trp Thr Phe
1               5                   10
```

<210> SEQ ID NO 56
<211> LENGTH: 9
<212> TYPE: PRT
<213> ORGANISM: Artificial Sequence
<220> FEATURE:
<223> OTHER INFORMATION: Chemically synthesized

<400> SEQUENCE: 56

```
Gly Gly Gly Thr Lys Leu Glu Ile Lys
1               5
```

<210> SEQ ID NO 57
<211> LENGTH: 336
<212> TYPE: DNA
<213> ORGANISM: Artificial Sequence
<220> FEATURE:
<223> OTHER INFORMATION: Chemically synthesized

<400> SEQUENCE: 57

```
gaggttcagc tgcagcagtc tggggcagag cttgtgaggt caggggcctc agtcaagttg      60
tcctgcacag cttctggctt caacattaaa gactactata tgcactgggt taagcagagg     120
cctgaacagg gcctggagtg gattggatgg tttgatcctg agaatggtga tgctgaatat     180
gccccgaagt tccaggacaa ggccactatg actgcagaca tcctccaa cgcagcctac       240 ctgcagctca gcagcctgac atctgaggac actgccgtct attactgtaa tggttatctt     300
tactggggcc aagggactct ggtcactgtc tcttca                               336
```

<210> SEQ ID NO 58
<211> LENGTH: 112
<212> TYPE: PRT
<213> ORGANISM: Artificial Sequence
<220> FEATURE:
<223> OTHER INFORMATION: Chemically synthesized

<400> SEQUENCE: 58

```
Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
```

-continued

```
           20              25              30

Tyr Met His Trp Val Lys Gln Arg Pro Glu Gln Gly Leu Glu Trp Ile
       35              40              45

Gly Trp Phe Asp Pro Glu Asn Gly Asp Ala Glu Tyr Ala Pro Lys Phe
   50              55              60

Gln Asp Lys Ala Thr Met Thr Ala Asp Thr Ser Ser Asn Ala Ala Tyr
65              70              75              80

Leu Gln Leu Ser Ser Leu Thr Ser Glu Asp Thr Ala Val Tyr Tyr Cys
               85              90              95

Asn Gly Tyr Leu Tyr Trp Gly Gln Gly Thr Leu Val Thr Val Ser Ser
           100             105             110
```

```
<210> SEQ ID NO 59
<211> LENGTH: 336
<212> TYPE: DNA
<213> ORGANISM: Artificial Sequence
<220> FEATURE:
<223> OTHER INFORMATION: Chemically synthesized

<400> SEQUENCE: 59
gatgttttga tgacccaaac tccactctcc ctgcctgtca gtcttggaga tcaagcctcc      60
atctcttgca gatctagtca gaacattgta cataataatg gaaacaccta tttagaatgg     120
taccttcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggaatt tattactgct ttcaaggttc acatgttccg     300
cacacgttcg gagggggggac caggctggaa ataaaa                              336
```

```
<210> SEQ ID NO 60
<211> LENGTH: 112
<212> TYPE: PRT
<213> ORGANISM: Artificial Sequence
<220> FEATURE:
<223> OTHER INFORMATION: Chemically synthesized

<400> SEQUENCE: 60
```

```
Asp Val Leu Met Thr Gln Thr Pro Leu Ser Leu Pro Val Ser Leu Gly
1               5              10              15

Asp Gln Ala Ser Ile Ser Cys Arg Ser Ser Gln Asn Ile Val His Asn
           20              25              30

Asn Gly Asn Thr Tyr Leu Glu Trp Tyr Leu Gln Lys Pro Gly Gln Ser
       35              40              45

Pro Lys Leu Leu Ile Tyr Lys Val Ser Asn Arg Phe Ser Gly Val Pro
   50              55              60

Asp Arg Phe Ser Gly Ser Gly Ser Gly Thr Asp Phe Thr Leu Lys Ile
65              70              75              80

Ser Arg Val Glu Ala Glu Asp Leu Gly Ile Tyr Tyr Cys Phe Gln Gly
               85              90              95

Ser His Val Pro His Thr Phe Gly Gly Gly Thr Arg Leu Glu Ile Lys
           100             105             110
```

```
<210> SEQ ID NO 61
<211> LENGTH: 339
<212> TYPE: DNA
<213> ORGANISM: Artificial Sequence
<220> FEATURE:
<223> OTHER INFORMATION: Chemically synthesized

<400> SEQUENCE: 61
```

-continued

```
caggtccaac tgcagcagcc tgggctgag ctggtgaggc ctggggcttc agtgaaactg      60
tcctgcaagg cttctggcta catcttcacc acctactgga tgaactgggt gaagcagagg     120
cctggacagg gccttgaatg gattgctatg attgatcctt cagacagtga aactcactac     180
aatcaaatgt tcaaggacaa ggccacattg actgtagaca tcctccag cacggcctac      240 atgcagctca gcggcctgac atctgaagac tctgcggtct attactgtgc aagagggaa     300 ggctactggg gccaaggcac cactctcaca gtctcctca                          339
```

<210> SEQ ID NO 62
<211> LENGTH: 113
<212> TYPE: PRT
<213> ORGANISM: Artificial Sequence
<220> FEATURE:
<223> OTHER INFORMATION: Chemically synthesized

<400> SEQUENCE: 62

```
Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ile Phe Thr Thr Tyr
            20                  25                  30

Trp Met Asn Trp Val Lys Gln Arg Pro Gly Gln Gly Leu Glu Trp Ile
        35                  40                  45

Ala Met Ile Asp Pro Ser Asp Ser Glu Thr His Tyr Asn Gln Met Phe
    50                  55                  60

Lys Asp Lys Ala Thr Leu Thr Val Asp Thr Ser Ser Ser Thr Ala Tyr
65                  70                  75                  80

Met Gln Leu Ser Gly Leu Thr Ser Glu Asp Ser Ala Val Tyr Tyr Cys
                85                  90                  95

Ala Arg Gly Glu Gly Tyr Trp Gly Gln Gly Thr Thr Leu Thr Val Ser
            100                 105                 110

Ser
```

<210> SEQ ID NO 63
<211> LENGTH: 336
<212> TYPE: DNA
<213> ORGANISM: Artificial Sequence
<220> FEATURE:
<223> OTHER INFORMATION: Chemically synthesized

<400> SEQUENCE: 63

```
gatgttgtga tgacccagac tccactcact ttgtcggtta ccattggaca accagcctcc     60
atctcttgca agtcaagtca gagcctctta gatagtgatg gaaagacata tttgaattgg    120
ttgttacaga gccaggcca gtctccaaag cgcctaatct tcctggtgtc taaactggac     180
tctggagtcc ctgacaggtt cactggcagt ggatcaggga cagatttcac actgaaaatc     240
agcagagtgg aggctgagga tttgggagtt tattattgct ggcaaggtac acattttccg     300
tggacgttcg gtggaggcac caagctggaa atcaaa                              336
```

<210> SEQ ID NO 64
<211> LENGTH: 112
<212> TYPE: PRT
<213> ORGANISM: Artificial Sequence
<220> FEATURE:
<223> OTHER INFORMATION: Chemically synthesized

<400> SEQUENCE: 64

```
Asp Val Val Met Thr Gln Thr Pro Leu Thr Leu Ser Val Thr Ile Gly
```

-continued

```
1                 5                 10                15

Gln Pro Ala Ser Ile Ser Cys Lys Ser Ser Gln Ser Leu Leu Asp Ser
            20                    25                    30

Asp Gly Lys Thr Tyr Leu Asn Trp Leu Leu Gln Ser Pro Gly Gln Ser
        35                    40                    45

Pro Lys Arg Leu Ile Phe Leu Val Ser Lys Leu Asp Ser Gly Val Pro
    50                    55                    60

Asp Arg Phe Thr Gly Ser Gly Ser Gly Thr Asp Phe Thr Leu Lys Ile
65                    70                    75                    80

Ser Arg Val Glu Ala Glu Asp Leu Gly Val Tyr Tyr Cys Trp Gln Gly
                85                    90                    95

Thr His Phe Pro Trp Thr Phe Gly Gly Gly Thr Lys Leu Glu Ile Lys
            100                   105                   110
```

```
<210> SEQ ID NO 65
<211> LENGTH: 57
<212> TYPE: DNA
<213> ORGANISM: Artificial Sequence
<220> FEATURE:
<223> OTHER INFORMATION: Chemically synthesized

<400> SEQUENCE: 65
atgaaatgca gctgggtcat cttcttcctg atggcagtgg ttataggaat caattca          57
```

```
<210> SEQ ID NO 66
<211> LENGTH: 19
<212> TYPE: PRT
<213> ORGANISM: Artificial Sequence
<220> FEATURE:
<223> OTHER INFORMATION: Chemically synthesized

<400> SEQUENCE: 66

Met Lys Cys Ser Trp Val Ile Phe Phe Leu Met Ala Val Val Ile Gly
1                 5                 10                15

Ile Asn Ser
```

```
<210> SEQ ID NO 67
<211> LENGTH: 57
<212> TYPE: DNA
<213> ORGANISM: Artificial Sequence
<220> FEATURE:
<223> OTHER INFORMATION: Chemically synthesized

<400> SEQUENCE: 67
atgaagttgc ctgttaggct gttggtgctg atgttctgga ttcctgcttc cagcagt          57
```

```
<210> SEQ ID NO 68
<211> LENGTH: 19
<212> TYPE: PRT
<213> ORGANISM: Artificial Sequence
<220> FEATURE:
<223> OTHER INFORMATION: Chemically synthesized

<400> SEQUENCE: 68

Met Lys Leu Pro Val Arg Leu Leu Val Leu Met Phe Trp Ile Pro Ala
1                 5                 10                15

Ser Ser Ser
```

```
<210> SEQ ID NO 69
<211> LENGTH: 441
<212> TYPE: PRT
<213> ORGANISM: Artificial Sequence
```

-continued

```
<220> FEATURE:
<223> OTHER INFORMATION: Chemically synthesized

<400> SEQUENCE: 69

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400
```

-continued

```
Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
            435                 440
```

MONOCLONAL ANTIBODIES AGAINST PATHOLOGICAL TAU, AND METHODS OF DETECTION THEREOF

CROSS-REFERENCE TO RELATED APPLICATIONS

The present application is a 35 U.S.C. § 371 national phase application of, and claims priority to, International Application No. PCT/US2021/034056, filed May 25, 2021, which claims priority under 35 U.S.C. § 119(e) to U.S. Provisional Patent Application No. 63/029,977, filed May 26, 2020, all of which are is incorporated herein by reference in their entireties.

STATEMENT REGARDING FEDERALLY SPONSORED RESEARCH OR DEVELOPMENT

This invention was made with government support under AG017586, AG053036, AG010124, and AG062418 awarded by the National Institutes of Health. The government has certain rights in the invention

BACKGROUND

The neuropathological hallmarks of Alzheimer's Disease (AD) comprise extracellular amyloid-beta (Aβ) plaques and intraneuronal tau protein aggregates (inclusions) manifesting as neuritic plaques (NPs), neuropil threads (NTs), and neurofibrillary tangles (NFTs). Tau is a natively unstructured microtubule-associated protein expressed in the central nervous system as six differentially-spliced isoforms containing either 0, 1, or 2 N-terminal acidic exons and 3 or 4 microtubule-binding repeats (MTBRs). The typically unstructured tau protein can adopt a misfolded beta-sheet conformation that aggregates into fibrils with a filament core comprised of the MTBRs and folding that enables contact of the N-terminus with the core domains, to form paired helical filaments (PHFs) that assemble into NFTs. Accumulations of tau protein closely correlate with cognitive decline and neuron death in AD patients more so than the presence of Aβ plaques. Although there are no mutations in the gene encoding tau protein associated with AD, mutation of the tau (MAPT) gene results in Frontotemporal Dementia with Parkinsonism linked to chromosome 17 (FTDP-17). Furthermore, tau forms intracellular inclusions in additional neurodegenerative tauopathies such as fronto-temporal lobar degeneration with tau (FLTD-tau) including Pick's disease, progressive supranuclear palsy, and corticobasal degeneration. Therefore, tau plays a central role in the neurodegenerative disease process and presents an attractive target for therapeutic intervention in AD and related tauopathies.

Tau aggregates propagate throughout the brain in a stereotypical spatiotemporal pattern that progresses with disease severity, beginning in the locus coeruleus and transentorhinal cortex, followed by the hippocampus and neocortex, and reaching the visual cortex at the latest disease stages. Growing evidence suggests this process is mediated by cell-to-cell transmission of pathological tau seeds from a neuron containing fibrillar tau species to a normal recipient neuron. Release of monomeric tau and polymeric misfolded tau from neurons may result from cell death or neuronal activity, generating both free extracellular tau and a small percentage of vesicle encapsulated tau. Once taken up into a recipient neuron, pathological tau seeds act as a template to recruit native cellular tau into newly formed oligomers and fibrils. Mouse models have demonstrated that intracerebral injection of either synthetic tau preformed fibrils (PFFs) or human AD-brain-derived pathological tau (AD-tau) can instigate tau pathology in regions of the brain distant from the injection site in either transgenic (Tg) mice expressing mutant human tau or non-transgenic wildtype (WT) mice. Together, these findings provide impetus for the development of anti-tau antibodies as immunotherapeutics for AD based on the hypothesis that antibody binding to extracellular tau prevents spread of pathological tau aggregates throughout the brain. There is thus a need for novel agents that can be used for treating, ameliorating, and/or preventing AD, based in one aspect on neutralizing pathological tau. This disclosure addresses and meets those needs.

BRIEF SUMMARY

In one aspect, the present disclosure provides an isolated monoclonal antibody comprising a light chain variable region (VL) and a heavy chain variable region (VH), wherein the VL comprises a CDR1 region comprising the amino acid sequence of SEQ ID NOs: 23 or 51: a CDR2 region comprising the amino acid sequence of SEQ ID NOs: 25 or 53; and a CDR3 region comprising the amino acid sequence of SEQ ID NOs: 27 or 55, and wherein the VH comprises a CDR1 region comprising the amino acid sequence of SEQ ID NOs: 9 or 37: a CDR2 region comprising the amino acid sequence of SEQ ID NOs: 11 or 39; and a CDR3 region comprising the amino acid sequence of SEQ ID NOs: 13 or 41.

In another aspect, the present disclosure provides a pharmaceutical composition comprising at least one monoclonal antibody of the disclosure and at least one pharmaceutical excipient.

In yet another aspect, the present disclosure provides an isolated polynucleotide comprising at least one of the nucleic acid sequences of SEQ ID NOs: 57, 59, 61, or 63.

In yet another aspect, the present disclosure provides a method of preventing, minimizing, and/or reversing fibrilization of native tau, the method comprising contacting the native tau with an effective amount of at least one isolated monoclonal antibody of the disclosure.

In yet another aspect, the present disclosure provides a method of preventing or minimizing transmission of pathological tau to a cell and/or uptake of pathological tau by a cell, the method comprising contacting the cell with an effective amount of at least one isolated monoclonal antibody of the disclosure.

In yet another aspect, the present disclosure provides a method of reducing and/or preventing further increase in any intraneuronal tau aggregates or inclusions in a subject, the method comprising administering to the subject a therapeutically effective amount of at least one isolated monoclonal antibody of the disclosure.

In yet another aspect, the present disclosure provides a method of treating, preventing, and/or ameliorating a tauopathy in a subject, the method comprising administering to the subject a therapeutically effective amount of at least one isolated monoclonal antibody of the disclosure.

In yet another aspect, the present disclosure provides a method of detecting a tauopathy in a subject, the method comprising administering to the subject at least one labeled isolated monoclonal antibody of the disclosure, and detecting presence or absence of a complex of the at least one labeled isolated monoclonal antibody with any pathological tau present in the subject, wherein, if the complex is detected, the subject has a tauopathy.

In yet another aspect, the present disclosure provides a method of detecting pathological tau in a sample, the method comprising contacting the sample with at least one labeled isolated monoclonal antibody of the disclosure, and detecting presence or absence of a complex of the at least one labeled isolated monoclonal antibody with any pathological tau present in the sample, wherein, if the complex is detected, pathological tau are present in the sample.

In yet another aspect, the present disclosure provides an isolated monoclonal antibody, or fragment thereof, which recognizes a conformational epitope comprising amino acids 151-244 and amino acids 369-441 of pathological tau, and which affinity for pathological tau is higher than for native tau.

In yet another aspect, the present disclosure provides an autonomously replicating or an integrative mammalian cell vector comprising a recombinant nucleic acid encoding an antibody comprising a light chain variable region (VL) and a heavy chain variable region (VH), wherein the VL comprises a CDR1 region comprising the amino acid sequence of SEQ ID NOs: 23 or 51: a CDR2 region comprising the amino acid sequence of SEQ ID NOs: 25 or 53; and a CDR3 region comprising the amino acid sequence of SEQ ID NOs: 27 or 55, and wherein the VH comprises a CDR1 region comprising the amino acid sequence of SEQ ID NOs: 9 or 37: a CDR2 region comprising the amino acid sequence of SEQ ID NOs: 11 or 39; and a CDR3 region comprising the amino acid sequence of SEQ ID NOs: 13 or 41.

In yet another aspect, the present disclosure provides an isolated host cell comprising any least one vector of the disclosure.

BRIEF DESCRIPTION OF THE DRAWINGS

The following detailed description of specific embodiments of the disclosure will be better understood when read in conjunction with the appended drawings. For the purpose of illustrating the disclosure, the drawings show specific embodiments. It should be understood, however, that the disclosure is not limited to the precise arrangements and instrumentalities of the embodiments shown in the drawings.

FIG. 1A: Sandwich ELISA assay comprised of total tau capture antibody KOJA and three distinct tau antigens, AD-tau, AD-P1 PFFs, and tau monomer, detected by novel tau mAbs DMR7 or SKT82 and total tau antibody Tau5 as a loading control demonstrating similar levels of captured antigen for each form of tau. FIG. 1B: Dot blot assay of AD-tau and tau monomer immobilized onto nitrocellulose membrane without treatment or denatured by guanidine hydrochloride and heat treatment. Total tau immunoblotted by KOJA shows similar levels of tau immobilization. DMR7 and SKT82 selectively detect AD-tau compared to monomer and binding is diminished by denaturation, demonstrating that the conformation of pathological AD-tau is responsible for enhanced binding.

FIG. 3A: Western blot of tau fragments with DMR7 and SKT82 reveal distinct partial binding patterns to tau fragments. DMR7 and SKT82 detect full length tau isoforms T44, T43, and T44, but not the microtubule binding domain, K18. Loss of the C-terminus in the ABP construct and loss of the proline rich domain in the ΔK18-P construct reduce binding of DMR7 and SKT82, demonstrating a proline-rich domain and c-terminal epitope. Equal loading of tau protein fragments was determined by Coomassie blue stained gel and K9JA total tau antibody, which does not detect the ABP fragment. FIG. 3B: Schematic of tau constructs and tau mAb binding.

FIGS. 4A-4C: Tau mAbs inhibit AD-tau seeded aggregation of endogenous mouse tau in primary neurons. FIG. 4A: Quantification of immunocytochemistry detection of AD-tau seeded insoluble mouse tau in primary neurons detected by the mouse-tau specific R2295M antibody. Statistical significance was determined relative to non-specific IgG control, using one-way ANOVA with Tukey's post-hoc analysis: $*p<0.05$, $***p<0.001$, n=3-4 biological replicates each consisting of 3 technical replicate wells per plate. FIG. 4B: Representative images of tau R2295M mouse tau antibody staining in primary neurons induced by AD-tau seeding. Tau5, DMR7, and SKT82 show inhibition of seeded tau pathology. FIG. 4C: Immunoprecipitation of tau from AD-tau extracts by IgG, SKT82, or DMR7. Bound and unbound fractions evaluated by western blot with total tau antibody (17025).

FIGS. 5A-5B: Tau mAbs inhibit uptake of tau seeds into primary neurons. FIG. 5A: Immunofluorescence of internalized tau fibrils labeled with pH-sensitive PHRODO™-red dye that fluoresces in acidic late endo/lysosomal compartments. Top panel: overlay of brightfield, pHR-T40) AD-P1 PFFs red channel, and DAPI nuclei blue channel. Bottom panel: pHR-T40 AD-P1 PFFs red channel converted to white for visualization. FIG. 5B: Quantification of fluorescent internalized PHRODO™-red-labeled tau fibrils. Non-specific mouse IgG1 control did not inhibit uptake of fibrils into neurons, whereas SKT82, DMR7, and positive control Tau5 antibody significantly inhibited the uptake of fibrils into neurons. One-way ANOVA with Tukey's post-hoc analysis $**p<0.01$ compared to IgG1 control n=4 biological replicates.

FIG. 6A: Quantification of immunofluorescent staining of hyperphosphorylated tau with AT8 antibody in hippocampal slice cultures treated with AD-tau and IgG control, SKT82, or DMR7. Unpaired t-test, $**p<0.005$, $*p<0.05$, n=6 comprised of three fields of view per slice for two independent hippocampal slices. FIG. 6B: Representative images of AT8 immunofluorescent staining of tau pathology induced in hippocampal slices by treatment with AD-tau and inhibition by tau mAbs.

FIG. 7: SKT82 and DMR7 inhibit tau pathology in vivo. FIG. 7A: IHC staining of hyperphosphorylated tau with the AT8 antibody reveals abundant tau pathology in AD-tau injected 5×FAD mice 3 months post-injection compared to PBS-injected mice. FIG. 7B: Quantification of AT8-positive area reveals treatment with SKT82 significantly reduced the amount of AT8-positive tau pathology on the ipsilateral side, and DMR7 and SKT82 significantly reduce tau pathology on the contralateral side. Each mAb treatment group was individually compared to the IgG control group by unpaired t-test n=11-23 mice/group, each point represents mean % positive AT8 area for 3-5 sections per mouse.

FIG. 8A: Sequential extraction of soluble and sarkosyl-insoluble tau fractions from both ipsilateral and contralateral mouse hippocampi were evaluated for levels of hyperphosphorylated tau (PHF1) and total tau by immuno-blot. FIG. 8B: Quantification of immunoblots. Each mAb treatment group was individually compared to the IgG control group by unpaired t-test: *p<0.05 analyzed by unpaired t-test n=3-6 mice per group.

(FIG. 9A) Open field measurements of total activity and (FIG. 9B) Y-maze spontaneous alternations showed no difference between PBS controls and AD-tau-injected mice with IgG control or tau mAb treatment. Analyzed by One-way ANOVA. FIG. 9C: Contextual fear conditioning showed that 5×FAD mice learned well and demonstrate a conditioned freezing response upon training but no differences at 14-day remote recall. ***p<0.001 analyzed by two-tailed paired t-test.

DETAILED DESCRIPTION

Definitions

Figures 1A, 1B:
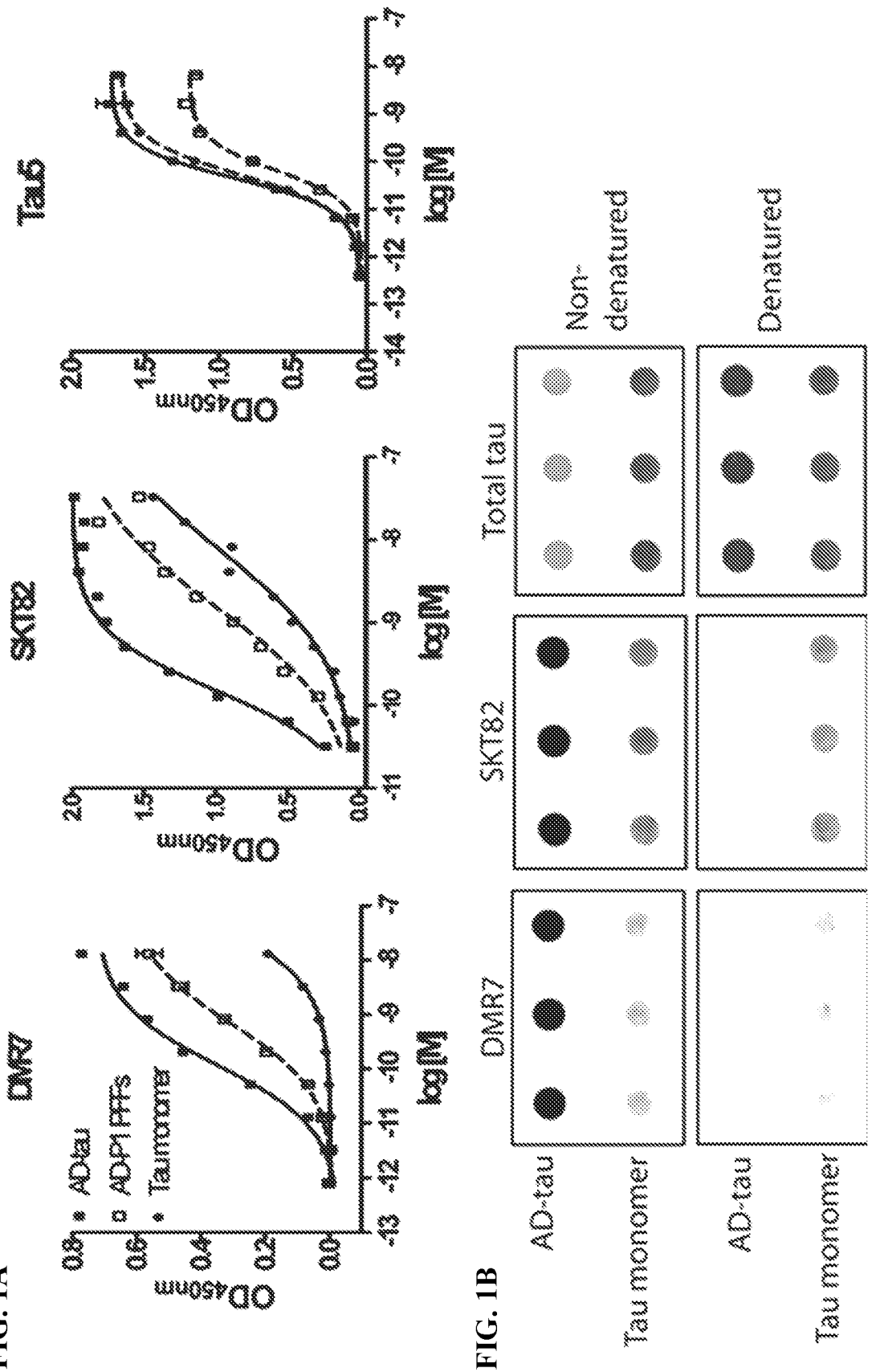
FIGS. 1A-1B: Novel tau mAbs selectively bind AD-tau compared to tau monomer.

Unless defined otherwise, all technical and scientific terms used herein have the same meaning as commonly understood by one of ordinary skill in the art to which the disclosure pertains. Although any methods and materials similar or equivalent to those described herein can be used in the practice for testing of the present disclosure, selected materials and methods are described herein. In describing and claiming the present disclosure, the following terminology will be used. It is also to be understood that the terminology used herein is for the purpose of describing particular embodiments only, and is not intended to be limiting.

As used herein, each of the following terms has the meaning associated with it in this section.

Unless defined otherwise, all technical and scientific terms used herein generally have the same meaning as commonly understood by one of ordinary skill in the art to which this disclosure belongs. Generally, the nomenclature used herein and the laboratory procedures in cell culture, molecular genetics, analytical chemistry, immunology, and nucleic acid chemistry and hybridization are those well-known and commonly employed in the art. Standard techniques or modifications thereof are used for chemical syntheses and chemical analyses.

The articles "a" and "an" are used herein to refer to one or to more than one (i.e. to at least one) of the grammatical object of the article. By way of example, "an element" means one element or more than one element.

As used herein, the term "Tau" or "tau" refers to a protein that promotes microtubule assembly and stability in cells. In certain embodiments, for the sake of illustration, the canonical sequence of tau is represented in SEQ ID NO: 69:

```
Isoform Tau-F (identifier: P10636-8)
Length: 441 amino acids; Molecular weight:
45,850 Da
          10         20         30         40
MAEPRQEFEV MEDHAGTYGL GDRKDQGGYT MHQDQEGDTD 50         60         70         80
AGLKESPLQT PTEDGSEEPG SETSDAKSTP TAEDVTAPLV 90        100        110        120
DEGAPGKQAA AQPHTEIPEG TTAEEAGIGD TPSLEDEAAG 130        140        150        160
HVTQARMVSK SKDGTGSDDK KAKGADGKTK IATPRGAAPP 170        180        190        200
GQKGQANATR IPAKTPPAPK TPPSSGEPPK SGDRSGYSSP 210        220        230        240
GSPGTPGSRS RTPSLPTPPT REPKKVAVVR TPPKSPSSAK 250        260        270        280
SRLQTAPVPM PDLKNVKSKI GSTENLKHQP GGGKVQIINK 290        300        310        320
KLDLSNVQSK CGSKDNIKHV PGGGSVQIVY KPVDLSKVTS 330        340        350        360
KCGSLGNIHH KPGGGQVEVK SEKLDFKDRV QSKIGSLDNI 370        380        390        400
THVPGGGNKK IETHKLTFRE NAKAKTDHGA EIVYKSPVVS 410        420        430        440
GDTSPRHLSN VSSTGSIDMV DSPQLATLAD EVSASLAKQG L
```

As used herein, the term "about" will be understood by persons of ordinary skill in the art and will vary to some extent on the context in which it is used. As used herein when referring to a measurable value such as an amount, a concentration, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "affinity" for a molecule towards another refers to the degree (or tightness) of binding between the two molecules. A higher affinity means tighter binding between the two molecules. Affinity can be quantified in terms of dissociation constant (or $K_d$), where a $K_d$ value that is lower in magnitude (closer to zero) indicates a higher affinity.

An "amino acid" as used herein is meant to include both natural and synthetic amino acids, and both D and L amino acids. "Standard amino acid" means any of the twenty L-amino acids commonly found in naturally occurring peptides. "Nonstandard amino acid residues" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides, and particularly at the carboxy- or amino-terminus, can be modified by methylation, amidation, acetylation or substitution with other chemical groups which can change a peptide's circulating half-life without adversely affecting activity of the peptide. Additionally, a disulfide linkage may be present or absent in the peptides.

The term "antibody," as used herein, refers to an immunoglobulin molecule able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present disclosure may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY: Harlow et al., 1989, Antibodies: A Laboratory Manual, Cold Spring Harbor, New York: Houston et al., 1988, Proc. Natl. Acad. Sci. USA 85:5879-5883: Bird et al., 1988, Science 242:423-426). As used herein, a "neutralizing antibody" is an immunoglobulin molecule that binds to and blocks the biological activity of the antigen.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present disclosure includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated or synthesized, or can be derived from a biological sample. Such a biological sample can include, but is not limited to a tissue sample, a tumor sample, a cell or a biological fluid.

A "coding region" of a gene consists of the nucleotide residues of the coding strand of the gene and the nucleotides of the non-coding strand of the gene that are homologous with or complementary to, respectively, the coding region of an mRNA molecule produced by transcription of the gene.

A "coding region" of an mRNA molecule also consists of the nucleotide residues of the mRNA molecule that are matched with an anti-codon region of a transfer RNA molecule during translation of the mRNA molecule or that encode a stop codon. The coding region may thus include nucleotide residues corresponding to amino acid residues not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "delivery vehicle" is used herein as a generic reference to any delivery vehicle capable of delivering a compound to a subject, including, but not limited to, dermal delivery vehicles and transdermal delivery vehicles.

The term "DNA" as used herein is defined as deoxyribonucleic acid.

"Effective amount" or "therapeutically effective amount" are used interchangeably herein, and refer to an amount of a compound, formulation, material, or composition, as described herein, effective to achieve a particular biological result. Such results may include, but are not limited to, treatment of a disease or condition as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, RNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment." as applied to a protein or peptide, refers to a subsequence of a larger protein or peptide. A "fragment" of a protein or peptide can be at least about 20 amino acids in length: for example at least about 50 amino acids in length: at least about 100 amino acids in length, at least about 200 amino acids in length, at least about 300 amino acids in length, and at least about 400 amino acids in length (and any integer value in between). As used herein, an antibody fragment refers to active fragments thereof, i.e., fragments having the same characteristics that are used for the definition of an antibody according to the disclosure, in certain embodiments higher affinity for pathological tau than for native (non-pathological tau). For convenience when the term antibody is used, fragments thereof exhibiting the same characteristic are also being considered.

As used herein, the term "fragment," as applied to a nucleic acid, refers to a subsequence of a larger nucleic acid. A "fragment" of a nucleic acid can be at least about 15 nucleotides in length: for example, at least about 50 nucleotides to about 100 nucleotides: at least about 100 to about 500 nucleotides, at least about 500 to about 1000 nucleotides, at least about 1000 nucleotides to about 1500 nucleotides: or about 1500 nucleotides to about 2500) nucleotides: or about 2500 nucleotides (and any integer value in between).

Conventional notation is used herein to describe polynucleotide sequences: the left-hand end of a single-stranded polynucleotide sequence is the 5'-end: the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand": sequences on the DNA strand which are located 5' to a reference point on the DNA are referred to as "upstream sequences": sequences on the DNA strand which are 3' to a reference point on the DNA are referred to as "downstream sequences."

An "individual", "patient" or "subject", as that term is used herein, includes a member of any animal species including, but are not limited to, birds, humans and other primates, and other mammals including commercially relevant mammals such as cattle, pigs, horses, sheep, cats, and dogs. Preferably, the subject is a human.

"Instructional material," as that term is used herein, includes a publication, a recording, a diagram, or any other medium of expression which can be used to communicate the usefulness of the composition and/or compound of the disclosure in a kit. The instructional material of the kit may, for example, be affixed to a container that contains the compound and/or composition of the disclosure or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron (s).

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T.

As used herein, the term "pathological tau" refers to a conformation, phosphorylated form, derivative, analogue, and/or modification of tau that forms and/or induces formation of paired helical filaments (PHFs), neuritic plaques (NPs), neuropil threads (NTs), and/or neurofibrillary tangles (NFTs). In certain embodiments, pathological tau plays a role in development of tauopathies, which are a class of neurodegenerative diseases involving the aggregation of tau protein into neurofibrillary or gliofibrillary tangles in the human brain. Non-limiting examples of Tauopathies include: Alzheimer's Disease, Pick's disease, Corticobasal degeneration, Argyrophilic grain disease (AGD), Primary age-related tauopathy (PART)/Neurofibrillary tangle-predominant senile dementia, Chronic traumatic encephalopathy (CTE), Progressive supranuclear palsy (PSP), Corticobasal degeneration (CBD), Frontotemporal dementia and parkinsonism linked to chromosome 17 (FTDP-17), Lyticobodig disease (Parkinson-dementia complex of Guam), Ganglioglioma and gangliocytoma. Meningioangiomatosis. Postencephalitic parkinsonism, Subacute sclerosing panencephalitis (SSPE), Lead encephalopathy, Tuberous sclerosis, Pantothenate kinase-associated neurodegeneration, and Lipofuscinosis.

As used herein, the term "pharmaceutical composition" refers to a mixture of at least one compound of the disclosure with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "protein", "peptide" and "polypeptide" are used interchangeably, and refer to a compound comprised of amino acid residues covalently linked by peptide bonds. The term "peptide bond" means a covalent amide linkage formed by loss of a molecule of water between the carboxyl group of one amino acid and the amino group of a second amino acid. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Proteins" include, for example, biologically active fragments, substantially homologous proteins, oligopeptides, homodimers, heterodimers, variants of proteins, modified proteins, derivatives, analogs, and fusion proteins, among others. The proteins include natural proteins, recombinant proteins, synthetic proteins, or a combination thereof. A protein may be a receptor or a non-receptor.

The term "recombinant DNA" as used herein is defined as DNA produced by joining pieces of DNA from different sources.

The term "recombinant polypeptide" as used herein is defined as a polypeptide produced by using recombinant DNA methods.

The term "RNA" as used herein is defined as ribonucleic acid.

The term "therapeutic" as used herein means a treatment and/or prophylaxis.

The term to "treat," as used herein, means reducing the frequency with which symptoms are experienced by a subject or administering an agent or compound to reduce the frequency and/or severity with which symptoms are experienced. As used herein, "alleviate" is used interchangeably with the term "treat."

As used herein, "treating a disease, disorder or condition" means reducing the frequency or severity with which a symptom of the disease, disorder or condition is experienced by a subject. Treating a disease, disorder or condition may or may not include complete eradication or elimination of the symptom.

The following abbreviations are used herein: AB, amyloid beta: AD, Alzheimer's disease: AD-tau, Alzheimer's brain derived tau: CBD, corticobasal degeneration: CDR, complementary-determining region: CNS, central nervous system: CSF, cerebrospinal fluid; DLB, dementia with Lewy bodies: ELISA, enzyme linked immunosorbent assay: IHC, immunohistochemistry: i.p., intraperitoneal: mAbs, monoclonal antibodies: MSA, multiple system atrophy: NFT, neurofibrillary tangles: nM, nanomolar: NP, neuritic plaque: NT, neuropil threads: PHF, paired helical filaments: PiD, Pick's disease: PSP, progressive supranuclear palsy: VH, heavy chain variable region: VL, light chain variable region: TBS, Tris buffered saline: tg, transgenic: WT, wildtype.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Based on the stereotypical pattern of pathological tau spread throughout the brain during AD progression, it is thought that tau undergoes cell-to-cell transmission in which portions of tau PHFs exit a cell and are taken-up into adjacent cells, wherein the seeds recruits naïve tau and templates the misfolded conformation thus propagating tau pathology.

The present disclosure is generally directed to certain anti-tau monoclonal antibodies (mAbs), or immunologically active fragments thereof, that selectively bind to pathological tau protein. In certain embodiments, the antibodies of the disclosure inhibit cell-to-cell transmission (spread) of pathological tau among cells. In certain embodiments, the antibodies of the disclosure can be used as immunotherapies for treatment of AD and FTLD-tau, among other tauopathies.

As described here, monoclonal mouse hybridoma cell lines were generated from murine spleen cells, and human SP2 myeloma cell lines and monoclonal populations were derived. DMR7 and SKT82 were identified as lead mAbs based on ELISA binding to AD PHFs, immunoprecipitation of tau from complex brain extracts, inhibition of seeded aggregation of tau in primary neuron models, and in vivo inhibition of pathological tau spread in mice (5×FAD) injected with AD brain derived tau. Without wishing to be limited by any theory, as a low proportion of peripherally administered IgG crosses the blood brain barrier, the selective targeting of pathological tau with conformation-selective antibodies reduces binding to non-pathological tau species, whereas high-affinity linear epitope tau antibodies can be sequestered by extracellular soluble tau present in the brain interstitial fluid.

In certain embodiments, the antibodies of the disclosure show preferential or selective binding towards the pathological form of tau compared to the native (non-pathological) form. In other embodiments, the antibodies of the disclosure reduce formation of pathological tau. In yet other embodiments, the antibodies of the disclosure detect pathological tau. In yet other embodiments, the antibodies of the disclosure are used as therapeutics for decreasing the development/spread of pathological tau.

In certain embodiments, the antibodies of the disclosure bind to pathological tau with a dissociation constant $K_d$ equal to or less than about $10^{-6}$ M, about $10^{-7}$ M, about $10^{-8}$ M, about $10^{-9}$ M, about $10^{-10}$ M, about $10^{-11}$, about $10^{-12}$, or about $10^{-13}$ M. In other embodiments, the antibodies of the disclosure bind to pathological tau with an affinity that at least about 1.5 times, 2 times, 2.5 times, 3 times, 4 times, 5 times, 6 times, 7 times, 8 times, 9 times, 10 times, 30 times, 100 times, 300 times, or 1000 times tighter (lower absolute $K_d$) than the affinity of the antibodies for native tau. In yet other embodiments, the antibodies of the disclosure bind to native tau with a dissociation constant $K_d$ equal to or higher than about $10^{-10}$ M, about $10^{-9}$ M, about $10^{-8}$ M, about $10^{-7}$ M, about $10^{-6}$ M, about $10^{-5}$ M, about $10^{-4}$ M, or about $10^{-3}$ M. In yet other embodiments, the antibodies of the disclosure bind with nearly equal affinity to native tau and pathological tau. Binding affinities of the antibodies can be determined by using a variety of methods recognized in the art, including methods described elsewhere herein, such as but not limited to isothermal calorimetry, surface plasmon resonance, immunoassay's such as ELISA or RIAs, and the like.

Compositions Comprising Antibodies

In one aspect, the disclosure comprises isolated monoclonal antibodies that selectively bind pathological tau over native tau.

In certain embodiments, the isolated monoclonal antibody, or fragment thereof, recognizes a conformational epitope comprising amino acids 151-244 and amino acids 369-441 of pathological tau, and its affinity for pathological tau is higher than for native tau. In other embodiments, the isolated monoclonal antibody, or fragment thereof, recognizes amino acids 120-151, 151-244, and 369-441 of pathological tau, and its affinity for pathological tau is higher than for native tau. In other embodiments, the isolated monoclonal antibody, or fragment thereof, recognizes amino acids 120-151 and 369-441 of pathological tau, and its affinity for pathological tau is higher than for native tau.

In certain embodiments, the antibody comprises a heavy chain. In other embodiments, the heavy chain comprises three complementary-determining regions (CDR), namely CDR1, CDR2, and CDR3. In other embodiments, the antibody comprises a light chain. In yet other embodiments, the light chain comprises three complementary-determining regions (CDR), namely CDR1, CDR2, and CDR3.

In certain embodiments, the monoclonal antibody comprises light and heavy variable chains having the sequences shown below:

```
SKT82 (sequencing performed by GenScript):
Heavy chain: DNA sequence (393 bp)
Signal sequence-FR1-CDR1-FR2-CDR2-FR3-CDR3 FR4, shown as:
SEQ ID NO: 65-SEQ ID NO: 1-SEQ ID NO: 2-SEQ ID NO: 3-SEQ ID
NO: 4-SEQ ID NO: 5-SEQ ID NO: 6-SEQ ID NO: 7
ATGAAATGCAGCTGGGTCATCTTCTTCCTGATGGCAGTGGTTATAGGAATCAATTCA

GAGGTTCAGCTGCAGCAGTCTGGGGCAGAGCTTGTGAGGTCAGGGGCCTCAGTCAAG

TTGTCCTGCACAGCTTCTGGCTTCAACATTAAAGACTACTATATGCACTGGGTTAAG

CAGAGGCCTGAACAGGGCCTGGAGTGGATTGGATGGTTTGATCCTGAGAATGGTGAT

GCTGAATATGCCCCGAAGTTCCAGGACAAGGCCACTATGACTGCAGACACATCCTCC

AACGCAGCCTACCTGCAGCTCAGCAGCCTGACATCTGAGGACACTGCCGTCTATTAC

TGTAATGGTTATCTTTACTGGGGCCAAGGGACTCTGGTCACTGTCTCTTCA

Heavy chain: Amino acid sequence (131 aa)
Signal sequence-FR1-CDR1-FR2-CDR2-FR3-CDR3-FR4, shown as:
SEQ ID NO: 66-SEQ ID NO: 8-SEQ ID NO: 9-SEQ ID NO: 10-SEQ ID
NO: 11-SEQ ID NO: 12-SEQ ID NO: 13-SEQ ID NO: 14
MKCSNVIFFIMAVVIGINSEVQLQQSGAELVRSGASVKLSCTASGFNIKDYYMHWVK

QRPEQGLEWIGWFDPENGDAEYAPKFQDKATMTADTSSNAAYLQLSSLTSEDTAVYY

CNGYLYWGQGTLVTVSS

Light chain: DNA sequence (393 bp)
Signal sequence-FR1-CDR1-FR2-CDR2-FR3-CDR3-FR4, shown as:
SEQ ID NO: 67-SEQ ID NO: 15-SEQ ID NO: 16-SEQ ID NO: 17-SEQ
ID NO: 18-SEQ ID NO: 19-SEQ ID NO: 20-SEQ ID NO: 21
ATGAAGTTGCCTGTTAGGCTGTTGGTGCTGATGTTCTGGATTCCTGCTTCCAGCAGT

GATGTTTTGATGACCCAAACTCCACTCTCCCTGCCTGTCAGTCTTGGAGATCAAGCC

TCCATCTCTTGCAGATCTAGTCAGAACATTGTACATAATAATGGAAACACCTATTTA

GAATGGTACCTTCAGAAACCAGGCCAGTCTCCAAAGCTCCTGATCTACAAAGTTTCC
```

-continued
AACCGATTTTCTGGGGTCCCAGACAGGTTCAGTGGCAGTGGATCAGGGACAGATTTC

ACACTCAAGATCAGCAGAGTGGAGGCTGAGGATCTGGGAATTTATTACTGCTTTCAA

GGTTCACATGTTCCGCACACGTTCGGAGGGGGGACCAGGCTGGAAATAAAA

```
Light chain: Amino acid sequence (131 aa)
Signal sequence-FR1-CDR1-FR2-CDR2-FR3-CDR3-FR4, shown as:
SEQ ID NO: 68-SEQ ID NO: 22-SEQ ID NO: 23-SEQ ID NO: 24-SEQ
ID NO: 25-SEQ ID NO: 26-SEQ ID NO: 27-SEQ ID NO: 28
```
*MKLPVRLLVLMFWIPASSS*DVLMTQTPLSLPVSLGDQASISCRSSQNIVHNNGNTYL

EWYLQKPGQSPKLLIYKVSNRFSGVPDRFSGSGSGTDFTLKISRVEAEDLGIYYCFQ

GSHVPHTFGGGTRLEIK

```
DMR7 (sequencing performed by LakePharma):
Heavy Chain: Nucleotide Sequence in FASTA format (MHC2825HC.2\;M13F)
FR1-CDR1-FR2-CDR2-FR3-CDR3-FR4, shown as:
SEQ ID NO: 29-SEQ ID NO: 30-SEQ ID NO: 31-SEQ ID NO: 32-SEQ
ID NO: 33-SEQ ID NO: 34-SEQ ID NO: 35
```
CAGGTCCAACTGCAGCAGCCTGGGGCTGAGCTGGTGAGGCCTGGGGCTTCAGTGAAA

CTGTCCTGCAAGGCTTCTGGCTACATCTTCACCACCTACTGGATGAACTGGGTGAAG

CAGAGGCCTGGACAGGGCCTTGAATGGATTGCTATGATTGATCCTTCAGACAGTGAA

ACTCACTACAATCAAATGTTCAAGGACAAGGCCACATTGACTGTAGACACATCCTCC

AGCACGGCCTACATGCAGCTCAGCGGCCTGACATCTGAAGACTCTGCGGTCTATTAC

TGTGCAAGAGGGGAAGGCTACTGGGGCCAAGGCACCACTCTCACAGTCTCCTCA

```
Heavy Chain: Amino Acid Sequence in FASTA format (MHC2825HC.2\;M13F)
FR1-CDR1-FR2-CDR2-FR3-CDR3-FR4, shown as:
SEQ ID NO: 36-SEQ ID NO: 37-SEQ ID NO: 38-SEQ ID NO: 39-SEQ
ID NO: 40-SEQ ID NO: 41-SEQ ID NO: 42
```
QVQLQQPGAELVRPGASVKLSCKASGYIFTTYWMNWVKQRPGQGLEWIAMIDPSDSE

THYNQMFKDKATLTVDTSSSTAYMQLSGLTSEDSAVYYCARGEGYWGQGTTLTVSS

```
Light Chain: Nucleotide Sequence in FASTA format (MHC2825LC.1\;M13F)
FR1-CDR1-FR2-CDR2-FR3-CDR3-FR4, shown as:
SEQ ID NO: 43-SEQ ID NO: 44-SEQ ID NO: 45-SEQ ID NO: 46-SEQ
ID NO: 47-SEQ ID NO: 48-SEQ ID NO: 49
```
GATGTTGTGATGACCCAGACTCCACTCACTTTGTCGGTTACCATTGGACAACCAGCC

TCCATCTCTTGCAAGTCAAGTCAGAGCCTCTTAGATAGTGATGGAAAGACATATTTG

AATTGGTTGTTACAGAGCCCAGGCCAGTCTCCAAAGCGCCTAATCTTCCTGGTGTCT

AAACTGGACTCTGGAGTCCCTGACAGGTTCACTGGCAGTGGATCAGGGACAGATTTC

ACACTGAAAATCAGCAGAGTGGAGGCTGAGGATTTGGGAGTTTATTATTGCTGGCAA

GGTACACATTTTCCGTGGACGTTCGGTGGAGGCACCAAGCTGGAAATCAAA

```
Light Chain: Amino Acid Sequence in FASTA format (MHC2825LC.1\;M13F)
FR1-CDR1-FR2-CDR2-FR3-CDR3-FR4, shown as:
SEQ ID NO: 50-SEQ ID NO: 51-SEQ ID NO: 52-SEQ ID NO: 53-SEQ
ID NO: 54-SEQ ID NO: 55-SEQ ID NO: 56
```
DVVMTQTPLTLSVTIGQPASISCKSSQSLLDSDGKTYLNWLLQSPGQSPKRLIFLVS

KLDSGVPDRFTGSGSGTDFTLKISRVEAEDLGVYYCWQGTHFPWTFGGGTKLEIK

Further combined sequences are provided herein:

| Combination sequence: | SEQ ID NO: |
| --- | --- |
| SKT82 VH DNA sequence:<br>SEQ ID NO: 1—SEQ ID NO: 2—SEQ ID NO: 3—SEQ ID<br>NO: 4—SEQ ID NO: 5—SEQ ID NO: 6—SEQ ID NO: 7 | SEQ ID<br>NO: 57 |
| SKT82 VH amino acid sequence:<br>SEQ ID NO: 8—SEQ ID NO: 9—SEQ ID NO: 10—SEQ ID<br>NO: 11—SEQ ID NO: 12—SEQ ID NO: 13—SEQ ID NO: 14 | SEQ ID<br>NO: 58 |
| SKT82 VL DNA sequence:<br>SEQ ID NO: 15—SEQ ID NO: 16—SEQ ID NO: 17—SEQ ID<br>NO: 18—SEQ ID NO: 19—SEQ ID NO: 20—SEQ ID NO: 21 | SEQ ID<br>NO: 59 |

-continued

| Combination sequence: | SEQ ID NO: |
|---|---|
| SKT82 VL amino acid sequence: SEQ ID NO: 22—SEQ ID NO: 23—SEQ ID NO: 24—SEQ ID NO: 25—SEQ ID NO: 26—SEQ ID NO: 27—SEQ ID NO: 28 | SEQ ID NO: 60 |
| DMR7 VH DNA sequence: SEQ ID NO: 29—SEQ ID NO: 30—SEQ ID NO: 31—SEQ ID NO: 32—SEQ ID NO: 33—SEQ ID NO: 34— SEQ ID NO: 35 | SEQ ID NO: 61 |
| DMR7 VH amino acid sequence: SEQ ID NO: 36—SEQ ID NO: 37—SEQ ID NO: 38—SEQ ID NO: 39—SEQ ID NO: 40—SEQ ID NO: 41—SEQ ID NO: 42 | SEQ ID NO: 62 |
| DMR7 VL DNA sequence: SEQ ID NO: 43—SEQ ID NO: 44—SEQ ID NO: 45—SEQ ID NO: 46—SEQ ID NO: 47—SEQ ID NO: 48—SEQ ID NO: 49 | SEQ ID NO: 63 |
| DMR7 VL amino acid sequence: SEQ ID NO: 50—SEQ ID NO: 51—SEQ ID NO: 52—SEQ ID NO: 53—SEQ ID NO: 54—SEQ ID NO: 55—SEQ ID NO: 56 | SEQ ID NO: 64 |

In certain embodiments, the antibody comprises an immunoglobulin light chain variable region (VL) comprising the amino acid sequence of SEQ ID NOs: 60 or 64.

In certain embodiments, the antibody comprises an immunoglobulin heavy chain variable region (VH) comprising the amino acid sequence of SEQ ID NOs: 58 or 62.

In certain embodiments, the antibody comprises an immunoglobulin light chain variable region (VL) comprising the amino acid sequence of SEQ ID NOs: 60 or 64, and an immunoglobulin heavy chain variable region (VH) comprising the amino acid sequence of SEQ ID NOs: 58 or 62.

In certain embodiments, the antibody comprises a VL comprising the amino acid sequence of SEQ ID NO: 60, and a VH comprising SEQ ID NO: 58. In other embodiments, the antibody comprises a VL comprising the amino acid sequence of SEQ ID NO: 64, and a VH comprising SEQ ID NO: 62.

In certain embodiments, the antibody comprises a VL comprising: a CDR1 region comprising the amino acid sequence of SEQ ID NOs: 23 or 51: a CDR2 region comprising the amino acid sequence of SEQ ID NOs: 25 or 53; and a CDR3 region comprising the amino acid sequence of SEQ ID NOs: 27 or 55.

In certain embodiments, the antibody comprises a VL comprising: a CDR1 region comprising the amino acid sequence of SEQ ID NO: 23: a CDR2 region comprising the amino acid sequence of SEQ ID NO: 25; and a CDR3 region comprising the amino acid sequence of SEQ ID NO: 27. In other embodiments, the antibody comprises a VL comprising: a CDR1 region comprising the amino acid sequence of SEQ ID NO: 51: a CDR2 region comprising the amino acid sequence of SEQ ID NO: 53; and a CDR3 region comprising the amino acid sequence of SEQ ID NO: 55.

In certain embodiments, the antibody comprises a VH comprising: a CDR1 region comprising the amino acid sequence of SEQ ID NOs: 9 or 37: a CDR2 region comprising the amino acid sequence of SEQ ID NOs: 11 or 39; and a CDR3 region comprising the amino acid sequence of SEQ ID NOs: 13 or 41.

In certain embodiments, the antibody comprises a VH comprising: a CDR1 region comprising the amino acid sequence of SEQ ID NO: 9: a CDR2 region comprising the amino acid sequence of SEQ ID NO: 11; and a CDR3 region comprising the amino acid sequence of SEQ ID NO: 13. In other embodiments, the antibody comprises a VH comprising: a CDR1 region comprising the amino acid sequence of SEQ ID NO: 37: a CDR2 region comprising the amino acid sequence of SEQ ID NO: 39; and a CDR3 region comprising the amino acid sequence of SEQ ID NO: 41.

In certain embodiments, the antibody comprises a VL comprising: a CDR1 region comprising the amino acid sequence of SEQ ID NO: 23: a CDR2 region comprising the amino acid sequence of SEQ ID NO: 25; and a CDR3 region comprising the amino acid sequence of SEQ ID NO: 27; and a VH comprising: a CDR1 region comprising the amino acid sequence of SEQ ID NO: 9: a CDR2 region comprising the amino acid sequence of SEQ ID NO: 11; and a CDR3 region comprising the amino acid sequence of SEQ ID NO: 13.

In certain embodiments, the antibody comprises a VL comprising: a CDR1 region comprising the amino acid sequence of SEQ ID NO: 51; a CDR2 region comprising the amino acid sequence of SEQ ID NO: 53; and a CDR3 region comprising the amino acid sequence of SEQ ID NO: 55; a VH comprising: a CDR1 region comprising the amino acid sequence of SEQ ID NO: 37; a CDR2 region comprising the amino acid sequence of SEQ ID NO: 39; and a CDR3 region comprising the amino acid sequence of SEQ ID NO: 41.

The disclosure further provides isolated polynucleotides (including RNA and/or DNA) encoding the antibodies or antigen binding fragments thereof, for example a nucleic acid encoding for one or more CDRs, or a variable heavy chain or variable light chain region of the antibodies of the disclosure. Nucleic acid includes DNA and RNA.

In certain embodiments, the antibody has a VL encoded by the nucleic acid sequence of SEQ ID NOs: 59 or 63. In other embodiments, the antibody has a VH encoded by the nucleic acid sequence of SEQ ID NOs: 57 or 61.

In certain embodiments, the disclosure provides an isolated polynucleotide comprising the nucleic acid sequence of SEQ ID NOs: 59 or 63. In other embodiments, he disclosure provides an isolated polynucleotide comprising the nucleic acid sequence of SEQ ID NOs: 57 or 61.

In certain embodiments, the disclosure provides an isolated polynucleotide comprising a nucleic acid encoding the amino acid sequence of SEQ ID NOs: 58 or 62. In other embodiments, the disclosure provides an isolated polynucleotide comprising a nucleic acid encoding the amino acid sequence of SEQ ID NOs: 60 or 64.

In certain embodiments, the disclosure provides an autonomously replicating or an integrative mammalian cell vector comprising a recombinant nucleic acid of the disclosure. In other embodiments, the disclosure provides a vector comprising a recombinant nucleic acid of the disclosure. In yet other embodiments, the recombinant nucleic acid of the disclosure encodes an antibody comprising a light chain variable region (VL) and a heavy chain variable region (VH), wherein the VL comprises a CDR1 region comprising the amino acid sequence of SEQ ID NOs: 23 or 51: a CDR2 region comprising the amino acid sequence of SEQ ID NOs: 25 or 53; and a CDR3 region comprising the amino acid sequence of SEQ ID NOs: 27 or 55, and wherein the VH comprises a CDR1 region comprising the amino acid sequence of SEQ ID NOs: 9 or 37: a CDR2 region comprising the amino acid sequence of SEQ ID NOs: 11 or 39; and a CDR3 region comprising the amino acid sequence of SEQ ID NOs: 13 or 41. In yet other embodiments, the vector comprises a plasmid or virus. In yet other embodiments, the vector comprises a mammalian cell expression vector. The expression vector can comprise nucleic acid sequences that direct and/or control expression of the inserted polynucleotide. Such nucleic acid sequences can include regulatory sequence, including promoter sequences, terminator sequences, polyadenylation sequences, and enhancer sequences. Systems for cloning and expression of a polypeptide in a variety of cells are well known in the art.

The disclosure further provides a host cell comprising the expression vector of the disclosure. In certain embodiments, the host cell is isolated. In other embodiments, the host cell is a non-human cell. In yet other embodiments, the host cell is mammalian.

The antibody of the disclosure can be a mammalian antibody, such as primate, human, rodent, rabbit, ovine, porcine or equine antibody. The antibody can be any class or isotype antibody, for example IgM or IgG. In certain embodiments, the antibody is IgG.

The disclosure further provides a kit comprising an antibody of the disclosure. The antibody may be an intact immunoglobulin molecule or fragment thereof such as Fab, F(ab)2 or Fv fragment. The antibody can be labelled as described elsewhere herein. The kit can be for use in a method of determining whether a subject has a neurodegenerative disease contemplated herein, and/or for treating a subject afflicted or thought to be afflicted with a neurodegenerative disease contemplated herein. The kit can further any other reagent or instrument that is required to implement a method of the disclosure, such as a buffer, an applicator, and the like.

In certain embodiments, the disclosure comprises pharmaceutical compositions comprising antibodies contemplated herein in combination with one or more pharmaceutically acceptable excipients. In some embodiments the pharmaceutical composition is formulated for parenteral delivery. In other embodiments, the antibodies are humanized.

Method of Treating a Tauopathy

In another aspect, the disclosure provides a method of treating a tauopathy comprising administering a therapeutically effective amount of an isolated monoclonal antibody of the disclosure to a patient. In certain embodiments, the antibody is humanized. In other embodiments, the antibody is administered as a pharmaceutical composition.

The monoclonal antibodies described above may be used to treat, prevent, and/or ameliorate tauopathies by inhibiting cell-to-cell transmission (spread) of pathological tau, as demonstrated herein. In certain embodiments, the tauopathies include but are not limited to Alzheimer's Disease, Pick's disease, Corticobasal degeneration, Argyrophilic grain disease (AGD), Primary age-related tauopathy (PART)/Neurofibrillary tangle-predominant senile dementia, Chronic traumatic encephalopathy (CTE), Progressive supranuclear palsy (PSP), Corticobasal degeneration (CBD), Frontotemporal dementia and parkinsonism linked to chromosome 17 (FTDP-17), Lytico-bodig disease (Parkinson-dementia complex of Guam), Ganglioglioma and gangliocytoma, Meningioangiomatosis, Postencephalitic parkinsonism, Subacute sclerosing panencephalitis (SSPE), Lead encephalopathy, Tuberous sclerosis, Pantothenate kinase-associated neurodegeneration, Lipofuscinosis, and any other pathological tau neurodegenerative disorders. The antibody can be administered systemically or directly to the site where pathological tau is observed or thought to be present. In a non-limiting example, the antibody can be administered by injection into a blood vessel supplying the brain or into the brain itself. The subject can be a mammal, such as a human or a non-human mammal.

Methods of Detecting a Tauopathy

In yet another aspect, the disclosure provides methods of detecting pathological tau and/or a tauopathy in a patient. In other embodiments, the antibodies of the disclosure can be used as diagnostic tools for neurodegenerative disorders associated with pathological tau, including but not limited to Alzheimer's Disease, Pick's disease, Corticobasal degeneration, Argyrophilic grain disease (AGD), Primary age-related tauopathy (PART)/Neurofibrillary tangle-predominant senile dementia, Chronic traumatic encephalopathy (CTE), Progressive supranuclear palsy (PSP), Corticobasal degeneration (CBD), Frontotemporal dementia and parkinsonism linked to chromosome 17 (FTDP-17), Lytico-bodig disease (Parkinson-dementia complex of Guam), Ganglioglioma and gangliocytoma, Meningioangiomatosis, Postencephalitic parkinsonism, Subacute sclerosing panencephalitis (SSPE), Lead encephalopathy, Tuberous sclerosis, Pantothenate kinase-associated neurodegeneration, Lipofuscinosis, and any other pathological tau neurodegenerative disorders.

In certain embodiments, the method of detecting pathological tau and/or a tauopathy in a subject comprises the steps of administering a labeled, isolated monoclonal antibody of the disclosure to the subject, and detecting the presence of absence of a complex between any pathological tau in the subject and the antibody. If the complex is present, that indicates that pathological tau exist in the subject. In certain embodiments, if pathological tau is present in the subject, the subject has a neurodegenerative disease. In other embodiments, if pathological tau is not present in the subject, the subject does not have a neurodegenerative disease. In yet other embodiments, if the subject has a neurodegenerative disease, the individual is counseled to undergo therapy and/or pharmacological treatment for the neurodegenerative disease. In yet other embodiments, if the subject has a neurodegenerative disease, the individual is provided therapy and/or pharmacological treatment for the neurodegenerative disease.

In certain embodiments, the method further comprises comparing the level of antibody/pathological tau complex formed in the subject with the level of antibody/pathological tau complex formed in a reference subject. The reference subject can be a subject known not to have pathological tau, a subject known to have detectable pathological tau, and/or a subject known to have a certain level of pathological tau. The reference subject can further be the same subject being treated or evaluated, but corresponding to an earlier pathological tau detection experiment, as a way to evaluate disease progression and/or treatment efficacy in the subject.

In yet another aspect, the disclosure provides methods of detecting pathological tau in a sample. In certain embodiments, the antibodies of the disclosure can be used as diagnostic tools for detecting the presence of pathological tau in a sample.

In certain embodiments, the method of detecting pathological tau in a sample (for example, from a subject) comprises the steps of contacting the sample with a labeled, isolated monoclonal antibody of the disclosure, and detecting the presence or absence of a complex between any pathological tau in the sample and the antibody. If the complex is detected, that indicates the presence of pathological tau in the sample. The sample can be, in non-limiting examples, cerebrospinal fluid (CSF), blood, urine, saliva, or tissues from brain, gut, colon, skin, or salivary gland. In certain embodiments, the sample is a CSF sample and/or a brain tissue sample. In other embodiments, the sample is used as is after being removed from the subject. In other embodiments, the sample is pre-treated being used within the present methods.

In certain embodiments, the method further comprises comparing the level of antibody/pathological tau complex formed in the sample with the level of antibody/pathological tau complex formed in a reference sample. The reference sample can be from a subject known not to have pathological tau, a subject known to have detectable pathological tau, and/or a subject known to have a certain level of pathological tau. The reference sample can further be from the same subject being treated or evaluated, but corresponding to an earlier pathological taudetection, as a way to evaluate disease progression and/or treatment efficacy in the subject.

In certain embodiments, the level of pathological tau detected in a subject or in a sample from a subject correlates with severity or progression of a neurodegenerative disease in the subject. In other embodiments, the methods of the disclosure can be used to monitor severity or progression of a neurodegenerative disease in the subject. In yet other embodiments, the methods of the disclosure can be used to monitor effectiveness of a therapy and/or pharmacological intervention in a subject afflicted or believed to be afflicted with a neurodegenerative disease.

Methods for detecting formation of a complex between the antibody and pathological tau comprise, but are not limited to, radioimmunoassay, enzyme-linked immunosorbant assay (ELISA), sandwich immunoassay, fluorescent immunoassay, precipitation reaction, gel immunodiffusion assay, agglutination assay, protein A immunoassay, immunoelectrophoresis assay, electrophoresis, western blotting, or any other technique known in the art.

The antibodies of the disclosure can be combined with a label and used to detect pathological tau in a patient or in a sample. Methods of labeling antibodies are known in the art and a variety of approaches may be employed. In certain embodiments the label is a radiolabel, such as but not limited to $F^{18}$, $I^{123}$, $In^{111}$, $I^{131}$, $C^{14}$, $H^3$, $Tc^{99m}$, $P^{32}$, $I^{125}$, $Ga^{68}$ and the like. In other embodiments, the label is a fluorescent label, such as but not limited to fluorescein, rhodamine and the like. In yet other embodiments, the label is a contrast agent, such as but not limited to gadolinium (Gd), dysprosium and iron, magnetic agents, and the like. Other labels include nuclear magnetic resonance active labels, positron emitting isotopes detectable by a PET scanner, chemiluminescent and enzymatic markers. Non-limiting imaging techniques include electron microscopy, confocal microscopy, light microscopy, positron emission tomography (PET), gamma-scintigraphy, magnetic resonance imaging (MRI), functional magnetic resonance imaging (FMRI), magnetoencephalography (MEG), and single photon emission computerized tomography (SPECT). In yet other embodiments, the label is on a secondary antibody that binds a primary antibody comprising the above described sequences.

22

Administration/Dosage/Formulations

Administration of the compounds and/or compositions of the present disclosure to a patient, preferably a mammal, more preferably a human, may be carried out using known procedures, at dosages and for periods of time effective to treating or preventing a disease or disorder and/or perform an imaging method contemplated in the disclosure. An effective amount of the therapeutic compound necessary for adequate disease or disorder treatment and/or imaging may vary according to factors such as the state of a disease or disorder in the patient: the age, sex, and weight of the patient; and the equipment used to detect the compound of the disclosure. One of ordinary skill in the art would be able to study the relevant factors and make the determination regarding the effective amount of the therapeutic and/or imaging compound without undue experimentation.

Actual dosage levels of the active ingredients in the pharmaceutical compositions of this disclosure may be varied so as to obtain an amount of the active ingredient that is effective to achieve successful disease or disorder treatment and/or imaging for a particular patient, composition, and mode of administration, without being toxic to the patient.

In certain embodiments, the compositions of the disclosure are formulated using one or more pharmaceutically acceptable excipients or carriers. In certain embodiments, the pharmaceutical compositions of the disclosure comprise an effective amount of a compound of the disclosure and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Compounds of the disclosure for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 3050 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40) mg to about 900 mg, about 50 mg to about 800 mg, about 60 mg to about 750 mg, about 70) mg to about 600 mg, about 80 mg to about 500 mg, and any and all whole or partial increments therebetween.

In certain embodiments, the dose of a compound of the disclosure is from about 1 mg and about 2,500 mg. In certain embodiments, a dose of a compound of the disclosure used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in certain embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like.

Routes of administration of any one of the compositions of the disclosure include oral, nasal, rectal, intravaginal, parenteral, buccal, sublingual or topical. The compounds for use in the disclosure may be formulated for administration by any suitable route, such as for oral or parenteral, for example, transdermal, transmucosal (e.g., sublingual, lingual, (trans) buccal, (trans) urethral, vaginal (e.g., trans- and perivaginally), (intra) nasal and (trans) rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In certain embodiments of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additional Administration Forms

Additional dosage forms of this disclosure include dosage forms as described in U.S. Pat. Nos. 6,340,475; 6,488,962; 6,451,808; 5,972,389; 5,582,837; and 5,007,790. Additional dosage forms of this disclosure also include dosage forms as described in U.S. Patent Applications Nos. 2003/0147952; 2003/0104062; 2003/0104053; 2003/0044466; 2003/0039688; and 2002/0051820. Additional dosage forms of this disclosure also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Experimental Examples

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, practice the claimed methods of the present disclosure. The following working examples therefore, specifically point out selected embodiments of the present disclosure, and are not to be construed as limiting in any way the remainder of the disclosure.

Materials & Methods

Extraction of AD-Tau:

Postmortem human brain tissue from neuropathologically confirmed AD cases were used for extraction of AD-tau. Briefly, gray matter from frontal cortex was homogenized in high salt buffer (10 mM Tris-HCl pH 7.4, 800 mM NaCl, 1 mM EDTA, 2 mM DTT, with a protease inhibitor cocktail and PMSF as well as 0.1% sarkosyl and 10% sucrose) in a dounce homogenizer in nine volumes of buffer per gram tissue. This was followed by centrifugation at 10,000 g for 10 min at 4° C. Sarkosyl was added to the pooled supernatant up to 1% and rotated 1 h at room temperature (RT) then centrifuged at 300,000 g for 1 h at 4° C. The sarkosyl-insoluble pellet, containing pathological tau, was washed in PBS at 100 μL/g gray matter, then resuspended in PBS by sonicating with 20 pulses at 0.5 sec/pulse using a hand-held QSonica probe and then centrifuged again at 45,000 g for 30 min at 4° C. The pellet was resuspended in one-fifth the previous PBS volume and sonicated with 20-60 pulses and centrifuged 10,000 g for 30 min at 4° C. The final supernatant contained enriched AD-tau at 5-20% purity. Total tau concentration was determined using a Tau5 ELISA assay (Guo & Lee, 2011, J. Biol. Chem. 286 (17): 15317-31).

Tau Expression, Purification, and Seeded Fibrillization:

Full length tau protein, T40 (2N4R) isoform, and fragments were expressed in BL21(DE3) RIL *E. coli* and purified by cation exchange chromatography (Li & Lee, 2006, Biochemistry 45 (51): 15692-701). AD-tau seeded recombinant tau PFFs (i.e., AD-P1 PFFs) were generated by incubation of 36 μM T40 tau (2N4R) with 4 μM AD-tau seeds comprising 10% of the fibrillization reaction with 2 mM DTT in PBS pH 7.0, with shaking at 1000 RPM for 3 days at 37° C. (Guo, et al., 2016, J. Experim. Med. 213 (12): 2635-54). The reaction mixture was centrifuged at 45,000 g for 30 min and fibrillized tau was collected in the pellet fraction, which was resuspended in the original reaction volume mixture.

Antibody Generation:

DMR7 and SKT82 hybridoma clones were generated as previously described for other tau mAbs (Gibbons, et al., 2018, J. Neuropathol. Experim. Neur. 77 (3): 216-28). Briefly, mice were injected subcutaneously with AD-tau in Freund's complete adjuvant, and spleens were dissociated and fused with SP2 myeloma cells with PEG treatment. Hybridoma clones were diluted with limiting dilutions and screened for tau antibody binding to T40 tau, AD-P1 PFFs, and AD-tau. Clones with selective binding to AD-P1 PFFs and AD-tau were prioritized and sub-cloned two times to ensure monoclonal populations. Antibodies were purified from hybridoma cell culture media using HiTrap MabSelect SuRe columns (GE Healthcare).

Sandwich ELISA:

Rabbit polyclonal anti-tau antibody K9JA (Dako) was coated onto 384-well MaxiSorp plates (Fisher Scientific) at 100 ng/well in 0.1 M sodium carbonate buffered to pH 9.6 at 4° C. overnight. Blocking was performed with BlockAce solution (Abd Serotec) at 4° C. overnight. Fibrillized tau antigens AD-P1 PFFs and AD-tau were sonicated, and then all tau antigens including T40 monomer were diluted to 0.2-0.8 μg/mL in 0.2% bovine serum albumin (BSA) in PBS and applied to K9JA-coated plates. Antigens were captured by total tau antibody K9JA at 4° C. overnight. Plates were washed with PBS containing 0.015% Tween-20 (PBST) and the novel mouse tau antibodies or Tau5 total tau control antibody were added to plates for 2 h at 22° C. Plates were washed with PBST and HRP-conjugated anti-mouse (Jackson Immunoresearch) secondary antibodies were applied for 2 h at 22° C. Plates were washed and tetramethylbenzidine peroxidase substrate (KPL laboratories) was added to wells to provide a colorimetric readout, quenched with 10% phosphoric acid and then absorbance measured at 450 nm (Molecular Devices SpectraMax).

Tau Denaturation and Immunoblots:

T40 tau monomer or AD-tau were chemically and thermally denatured by 1:10 dilution in 8M guanidine hydrochloride and heating at 100° C. for 15 min, and non-denatured controls were diluted in Tris-buffered saline (TBS) at RT. Denatured or non-denatured tau was then diluted 1:50 in TBS and applied to 0.2 μm nitrocellulose membrane using a vacuum apparatus. For western blots, tau isoforms and fragments were diluted in SDS sample buffer, heated 10 min at 100° C., run on 12.5% SDS-PAGE gels and transferred to 0.2 μm nitrocellulose membrane. Immunoblots and dot blots were probed with either total tau control antibody K9JA diluted to 2 μg/mL or conformation-selective mAbs diluted in 5% non-fat milk at 20 μg/mL at 4° C. Infrared dye labeled secondary antibodies (LiCor) were used to detect primary antibody binding, with analysis on a LiCor scanner (LiCor).

Immunohistochemistry (IHC):

All human brain tissue samples used in this study were obtained at autopsy, fixed in ethanol or paraformaldehyde, paraffin-embedded, and cut into 6 μm thick sections and characterized (Arnold, et al., 2013, J. Compar. Neurol. 521 (18): 4339-55: Toledo, et al., 2014, Alzheimer's & Dementia: J. Alzheimer's Association 10 (4): 477-84 e1). For IHC staining, sections were deparaffinized in xylene and rehydrated in ethanol (100-70%) (Gibbons, et al., 2018, J. Neuropathol. Experim. Neur. 77 (3): 216-28). Tau antibodies MC1 and PHF-1 (gift of Peter Davies) were diluted 1:1,000 and 1:5,000, respectively, while DMR7 and SKT82 were diluted to 2 μg/mL in 2% FBS in 50 mM Tris pH 7.2 and applied overnight to rehydrated tissue sections without antigen retrieval in a humidified chamber at 4° C. Antibody binding was detected by Vectastain Elite ABC Kit (Vector) followed by DAB peroxidase substrate (Vector) and counterstaining with Harris hematoxylin (ThermoFisher).

Seeded Aggregation of Tau in Primary Neurons:

Primary cortical neurons from E16-19 CD-1 WTmice were cultured in 96-well plates at a density of 17,500 cells/well. After 7 days in vitro (DIV 7), the cells were treated in triplicates with either SKT82, DMR7, or IgG with at concentrations of 3.3-26.7 nM and subsequently transduced with 0.125 μg of AD tau PHF per well. After 7 days of AD-tau and antibody treatment, neurons were maintained in growth factor-rich conditioned media until DIV 21. Cells were washed with PBS and soluble tau was extracted with 0.5% HDTA for 15 min at RT, followed by fixation with 4% PFA and 4% sucrose for 15 min at RT. Immunocytochemistry was performed with the mouse tau-specific R2295M (CNDR) antibody, fluorescently labeled with anti-rabbit secondary antibody, and DAPI to stain nuclei. Imaging was performed on an INCELL™ Analyzer 2200 microscope. The DAPI-positive cell count, and area and density of mouse tau pathology, were analyzed using the INCELL™ Developer Toolbox software. The final quantification was based on density×area of pathological insoluble mouse tau normalized to cell number by DAPI-positive nuclei.

Immunoprecipitation:

A mixture of Dynabeads conjugated with protein A and protein G were mixed with 10 μg purified DMR7, SKT82, or IgG control antibody and AD-tau containing 2 μg of tau protein and rotated 3 h at RT. A magnetic stand was used to sequester Dynabeads and supernatant was transferred to another tube as the unbound fraction. Beads were washed three times with PBS and bound proteins eluted with SDS sample buffer and heating at 100° C. for 10 min. Equal proportions of unbound reaction and eluted proteins were run on 10% SDS-PAGE gels, transferred to nitrocellulose membranes and immunoblotted with the rabbit polyclonal total tau antibody 17025 (CNDR in-house).

pH-Sensitive Tau Labeling and Cellular Uptake Experiments:

Purified recombinant T40 tau (2N4R) was labeled with the pH-sensitive fluorescent tag, PHRODO™ red succinimidyl ester (ThermoFisher). Fluorescently-labeled tau was termed pHR-T40 and used in an in vitro seeded fibrillization reaction consisting of 10% pHR-T40, 80% unlabeled T40, and 10% sonicated AD-tau seeds. The reaction was shaken at 1,000 RPM for 4 days at 37° C. and fibrils collected by centrifugation at 100,000 g for 30 min. Pelleted fibrils (AD-P1 pHR-T40), were resuspended in PBS, sonicated, and added to E16-E18 cultured cortical neurons at DIV7-10. After 24 h treatment with AD-P1 pHR-T40, live cells were treated with NucBlue to stain nuclei and internalized AD-P1 pHR-T40 was imaged on a Leica DMI6000 microscope or imaged and evaluated with an INCELL™ 2200.

In Vivo Assessment of Tau Transmission:

Four month old female 5×FAD mice were stereotaxically-injected with 2 μg AD-tau into the hippocampus (bregma: −2.5 mm; lateral: +2 mm; depth: −2.4 mm from the skull) (Gibbons, et al., 2017, J. Neurosci. 37 (47): 11485-94). Mice were injected (intraperitoneal or i.p.) with 60 mg/kg of tau mAbs or IgG control mAb 4 days prior to AD-tau injection, on the day of AD-tau injection, and weekly thereafter for 3 months. Upon completion of the dosing period, mice were transcardially perfused with 30 mL phosphate buffered saline (PBS) at 120 mL/h and brains were fixed in 4% paraformaldehyde overnight. Fixed brains were embedded into paraffin blocks and then sectioned into 6 μm sections. Every 20th section through the hippocampus was subjected to IHC staining with AT8 mAb (ThermoFisher) diluted at 0.04 μg/mL or alternatively with 50 μM X-34, an amyloid binding dye (Sigma Aldrich). Slides were scanned with a 20× objective using a LAMINA™ slide scanner (PerkinElmer). Brain regions were annotated and AT8 positive area was quantified using HALO® software (Indica Labs).

Sequential Extraction of Soluble and Insoluble Tau from Mouse Tissue:

Brains were separated into ipsilateral and contralateral hemispheres and hippocampus was dissected and flash frozen on dry ice and kept at −80° C. Tissue was homogenized by sonication in 9 volumes of HS-RAB buffer (100 mM MES, 1 mM EDTA, 0.5 mM $MgSO_4$, 1 mM DTT, 1 mM PMSF, 0.75 M NaCl, 20 mM NaF, pH 6.8) with protease inhibitors and phosphatase inhibitors. Homogenates were centrifuged at 45,000 g for 30 min at 4° C. and the supernatant was saved as the soluble fraction, while the pellet was resuspended in 9 volumes of HS-RAB buffer containing 1% Triton X-100. Samples were again centrifuged (45,000 g for 30 min at 4° C.) and the supernatants were discarded, while the pellet was resuspended in 9 volumes of HS-RAB buffer containing 1% sarkosyl and then rotated for 1 h at 22° C. Samples were centrifuged at 45,000 g for 45 min at 4° C., the supernatant discarded, and the pellet washed with 500 μL PBS. Samples were centrifuged (45,000 g 30 for min at 4° C.), the supernatant discarded, and the pellet was resuspended in PBS at a volume two-times the mass of the original tissue, and sonicated to resuspend as the insoluble fraction.

Behavioral Tests:

Open Field procedures were horizontal and vertical activity recorded with IR beam breaks during a 10 min trial. Data were acquired with a Photobeam Activity System (San Diego Instruments). The percent spontaneous alternation in the Y-maze was calculated as 100×[number of alternations/(total arm entries−2)] where arm entry was defined as all four paws placed inside an arm. For contextual fear conditioning, a mouse was placed in a conditioning chamber (Med Associate) within a sound-attenuating cabinet, and a 2-s, 1.75 mA foot shock was delivered at 148-150 s of a 180-s acquisition trial. Twenty-four hours after acquisition, mice were returned to the conditioning chamber for a 5 min recall trial to assess long-term memory. Fourteen days after acquisition, remote memory was also assessed with a second recall trial. All trials were digitally recorded. Time spent motionless was automatically assessed by FREEZ-ESCAN™ software (Clever Systems).

Statistical Analysis:

Statistical analyses were performed with GraphPad PRISM® software. Quantification of tau uptake in primary neurons and tau pathology in the seeded aggregation model in primary neurons and slice culture were evaluated by One-way ANOVA with Tukey's post-hoc analysis. Quantification of AT8 positive tau pathology was performed using the mean percentage of AT8 positive area in 3-5 sections per mouse. Initial IgG1 and IgG2a treated groups showed statistically insignificant differences using two-tailed unpaired Student's t tests and were combined for statistical power in analysis of IHC staining and immunoblots of soluble and insoluble tau. DMR7- or SKT82-treated mice were compared against the IgG group by two-tailed unpaired Student's t tests. Contextual fear conditioning measures of % freezing consisted of repeated measurements of the same mice at different time points and were analyzed by two-tailed paired t-test to campre changes from prestimulation to 24 h recall and 24 h recall to 14 day remote recall.

Example 1: Generation of Conformation-Selective Tau mAbs

Towards the goal of generating conformation-selective tau mAbs, mice were inoculated with human AD brain-derived extracts enriched in insoluble tau (AD-tau). Hybridoma clones generated from immunized mice were screened by sandwich ELISA to simultaneously assess binding of antibodies to tau monomer, AD-tau seeded recombinant tau preformed fibrils (AD-P1 PFFs), and AD-tau. The pan-tau antibody Tau5 served as a loading control to ensure equivalent capture of the three tau forms by the immobilized pan-tau K9JA antibody (FIG. 1A). Clones that bound AD-tau and AD-P1 PFFs with greater apparent affinity than tau monomer were prioritized and subsequently sub-cloned by limiting dilutions to monoclonal populations. Two novel tau mAbs, DMR7 and SKT82, were identified as demonstrating increased affinity to AD-tau and AD-P1 PFFs compared to tau monomer (FIG. 1A). Sandwich ELISA measures of DMR7 provided an $EC_{50}$ of 0.10±0.01 nM for AD-tau, 0.46±0.32 nM for AD-P1 PFFs and 12.0±7.9 nM for tau monomer, whereas SKT82 $EC_{50}$ values were 0.17±0.03 nM for AD-tau, 2.38±1.12 nM for AD-P1 PFFs, and 4.13±3.74 nM for tau monomer.

To assess whether conformational differences between AD-tau and tau monomer contributed to the differences observed by ELISA, AD-tau and tau monomer were chemically and thermally denatured prior to immobilization on dot blots and probing with the DMR7 and SKT82 mAbs (FIG. 1B). Consistent with the ELISA results, both DMR7 and SKT82 showed greater interaction with non-denatured AD-tau than tau monomer, with loading of total tau assessed by binding of the KOJA pan-tau antibody. Upon denaturation of tau, the signal for DMR7 and SKT82 binding to AD-tau was greatly diminished, whereas the tau monomer signal was unaffected. Denaturation did not reduce the immobilization of AD-tau or tau monomer, as evidenced by similar or even slightly greater binding of K9JA to denatured tau compared to non-denatured tau. This demonstrates that denaturation of the AD-tau conformation reduces binding of DMR7 and SKT82 and suggests that the selectivity observed by ELISA results from binding to the misfolded pathological conformation of AD-tau.

Example 2: Novel Tau mAbs Detect Pathological Tau in Various Tauopathies

Figure 2:
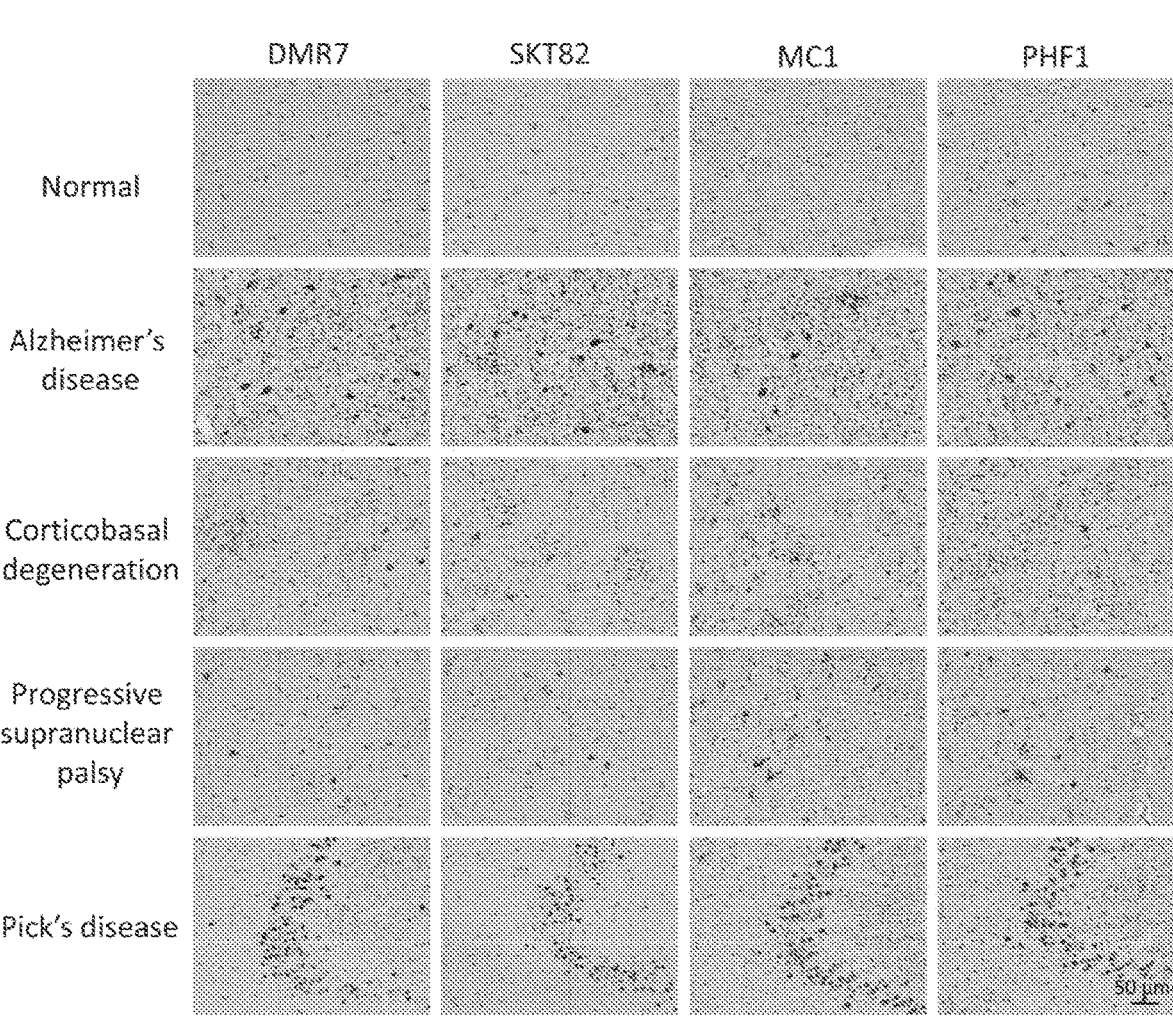
FIG. 2: Conformation-selective tau mAbs detect multiple human tauopathies. Immunohistochemical staining with novel conformation-selective tau mAbs, DMR7 and SKT82, conformation-selective control mAb MC1, and phospho-tau mAb PHF1, demonstrates binding of DMR7 and SKT82 to pathological tau in multiple human tauopathies but not brain tissue from cognitively normal control.

To determine whether DMR7 and SKT82 detect various forms of pathological tau, brain tissue from several human tauopathies, including AD, corticobasal degeneration (CBD), progressive supranuclear palsy (PSP), and Pick's disease (PiD), were analyzed by IHC. Both mAbs detected pathological tau lesions in all of the tauopathy brain sections to a similar extent as the diagnostic standard PHF1 antibody, which binds tau phosphorylated at Ser396 and Ser404 (FIG. 2). In AD midfrontal cortex, NFT, NP, and neuropil thread (NT) staining were readily detected by DMR7 and SKT82. In CBD cingulate cortex, astrocytic plaques and neuronal cell body pathology were detected by both mAbs. In PSP lentiform nucleus, glial astrocytic plaques and oligodendroglia coiled bodies were detected by DMR7 and SKT82, in addition to neuronal inclusions. Abundant round "Pick bodies" were readily detected in the dentate gyrus of PiD brain tissue by the two mAbs. Thus, both DMR7 and SKT82 differ from previously described conformation-preferring tau antibodies that selectively detected pathological tau in AD but not in other tauopathies. In fact. DMR7 and SKT82 staining of the various tauopathies resembles that observed with the well characterized conformation-selective antibody. MC1 (FIG. 2), which detected misfolded pathological tau in all four tauopathies. As growing in vivo and structural data demonstrate that different tauopathies are comprised of distinct conformational strains, these data demonstrate that DMR7 and SKT82 bind to a conformational epitope that is common among the tau strains found in the tauopathies tested here. Since the tau fibril cryo-EM structures to date primarily resolve the fibrillization core domain comprised of microtubule binding repeats, in certain embodiments the epitopes involved in the conformation-selective mAb binding are either shared among these different tau fibril structures or these different fibril structures have some flexibility that can accommodate mAb binding despite unique fibril core domains.

Example 3: DMR7 and SKT82 Bind a Conformational Epitope of Tau

Figure 3A:
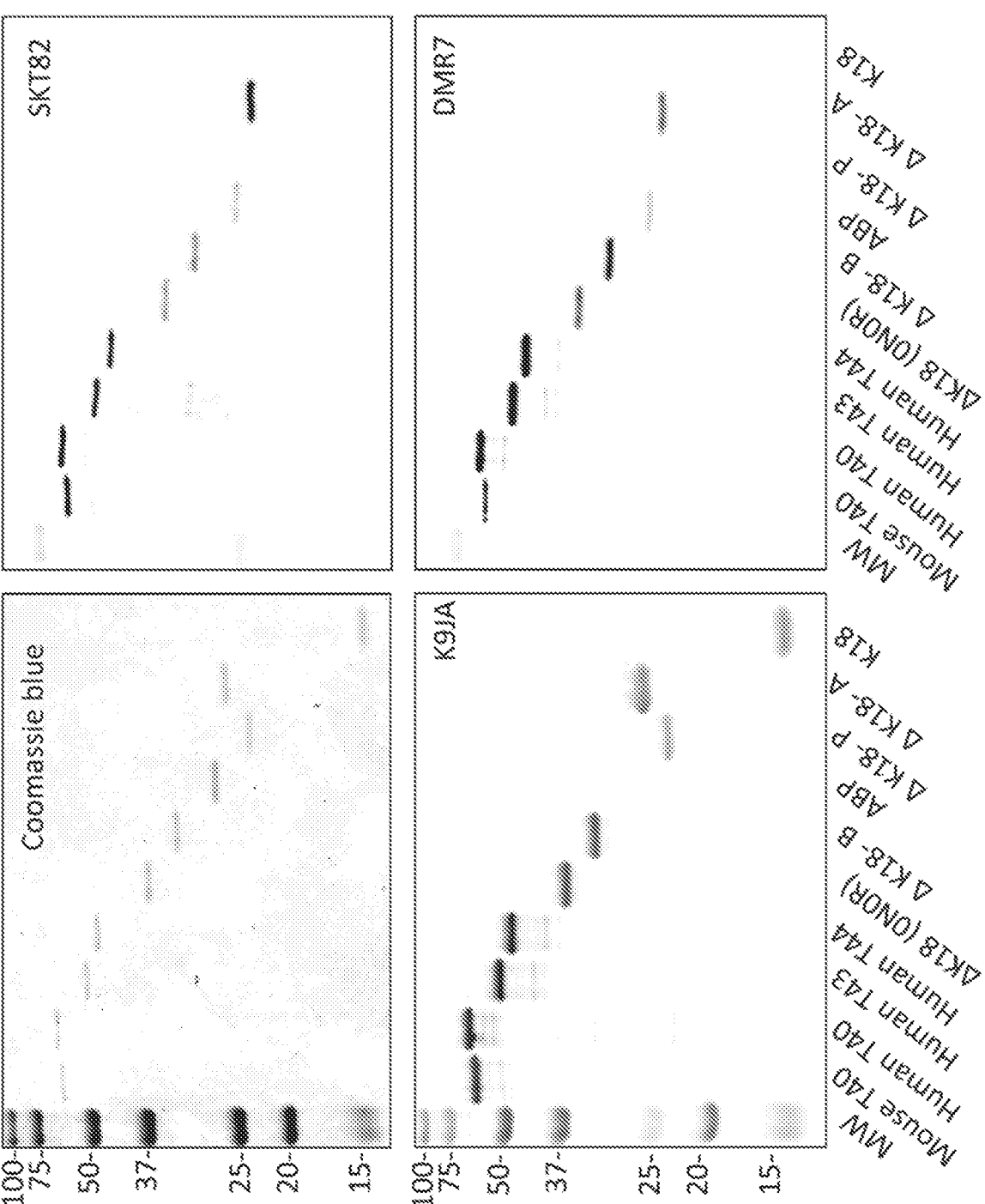
FIGS. 3A-3B: DMR7 and SKT82 bind to discontinuous epitopes of tau.
Figure 3B:
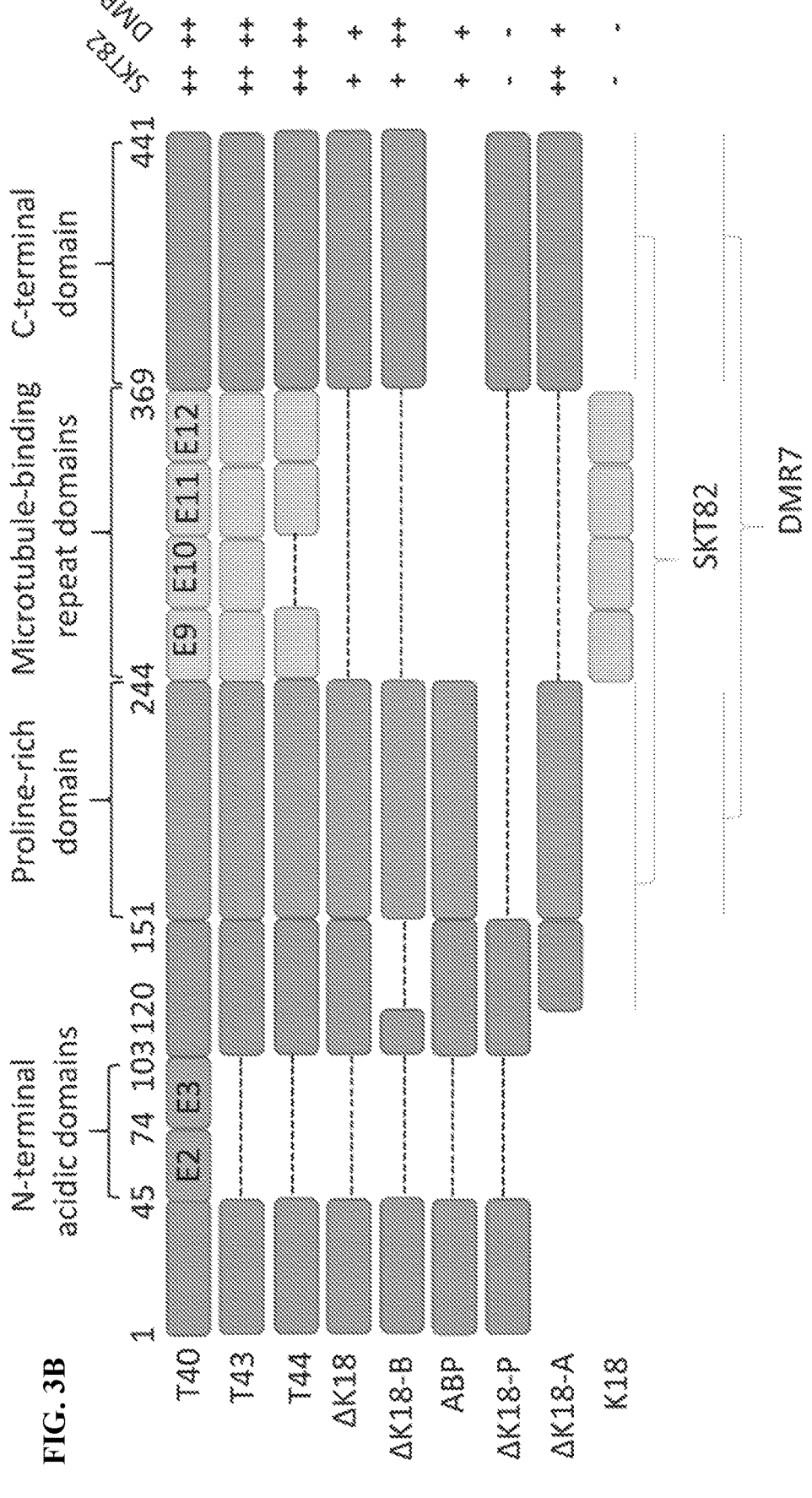

To gain insight into the nature of the conformation selectivity of DMR7 and SKT82, the epitope of these mAbs were investigated. DMR7 and SKT82 were able to detect full-length tau monomer by immunoblot even though they have a relatively low affinity for monomers by ELISA. Therefore, a panel of tau fragments were examined to identify those containing binding epitopes of DMR7 and SKT82 (FIG. 3A). Coomassie blue staining of the gels revealed comparable loading of all the tau fragments, which was further verified with the KOJA antibody with the exception of the ABP fragment, which is missing the K9JA C-terminal epitope. DMR7 detected all full-length tau isoforms including mouse tau but showed some selectivity for human T40 tau compared to mouse T40 tau, whereas SKT82 detected both full-length mouse and human tau isoforms similarly. Other than the slight differences in species selectivity. DMR7 and SKT82 have a number of similarities between their epitope profiles. Both tau mAbs failed to bind to the K18 fragment of tau, demonstrating the epitope is not in the MTBR region comprising the fibrillar core of tau PHFs (FIG. 3B). Consistent with this observation, both tau mAbs showed binding to the ΔK18 fragment which lacks the MTBRs; however, binding of both mAbs is slightly diminished compared to the binding of 4R tau isoforms. Deletion of the proline-rich domain between amino acids 151-244 (ΔK18-P) abolished binding of both mAbs, demonstrating an essential epitope within that region. The ABP fragment of tau, which contains the proline-rich region but lacks the C-terminus, also demonstrated greatly diminished binding by the mAbs, indicating that optimal mAb binding requires a C-terminal epitope in addition to the proline-rich domain epitope. Both DMR7 and SKT82 bound well to ΔK18-A, which lacks the N-terminus and MTBRs and consists of the basic region from 120-151, the proline rich domain, and the C-terminus. Comparison of the SKT82 signal between ΔK18-A and ΔK18-B suggests that SKT-82 may bind an epitope in the basic region from 120-151. Together, these findings indicate that DMR7 and SKT82 bind to conformational epitopes of tau comprised of the proline-rich domain containing amino acids 151-244 and a C-terminal epitope from amino acids 369-441. Additionally, SKT82 can have some binding contribution from the basic region containing amino acids 120-151.

Example 4: Tau mAbs Inhibit Seeded Fibrillization of Endogenous Tau in Primary Neurons To determine whether DMR7 and SKT82 binding to AD-tau would inhibit the seeding of tau aggregates in primary neurons in a previously described assay (Guo, et al., 2016, J. Experim. Med. 213 (12): 2635-54). WT mouse cortical neurons were treated with AD-tau to template fibrillization of endogenous cellular mouse tau into insoluble aggregates. Both DMR7 and SKT82 significantly reduced the seeding of pathological tau aggregates in a dose-dependent manner (FIGS. 4A-4B), with mouse tau pathology inhibited by 60.5±13.8% with DMR7 treatment and 82.2±8.3% by SKT82 addition. Both conformation-selective tau mAbs provided greater inhibition of AD-tau seeding in primary neurons than the pan-tau control antibody. Tau5. Non-specific mouse IgG control antibody did not inhibit cellular tau aggregates induced by AD-tau. Furthermore, both DMR7 and SKT82 immunoprecipitated tau from the complex protein mixture present in the AD-tau extracts (FIG. 4C), supporting the notion that conformation-selective tau mAbs inhibit seeded aggregation in tau primary neurons through direct sequestration of tau seeds.

Example 5: DMR7 and SKT82 Block Uptake of Labeled AD-P1 PFFs into Neurons

To elucidate the mechanism by which the conformation-selective tau mAbs inhibit seeding of cellular tau aggregates, recombinant tau protein was covalently-modified with the pH-sensitive PHRODO™-red fluorophore, which fluoresces in acidic conditions including late endosomal and lysosomal compartments. Fluorophore-labeled T40 tau (pHRT40) was fibrillized in the presence of 10% AD-tau seeds to template propagation of the AD fibril conformation (pHRT40) AD-P1 PFFs) and PHRODO™ fluorescence was monitored after pHRT40 AD-P1 PFF addition to primary neurons (FIG. 5A). Both SKT82 and DMR7 significantly inhibited uptake of pHRT40 AD-P1 PFFs into primary neurons, with the resulting fluorescence signal decreased by 66.1±20.8% and 61.5±9.7%, respectively (FIG. 5B). Without wishing to be limited by any theory, this finding supports a mechanism of SKT82 and DMR7 binding to pathological tau seeds and inhibiting uptake into recipient neurons.

Example 6: SKT82 Inhibits Tau Pathology in Slice Culture

Figure 6B:
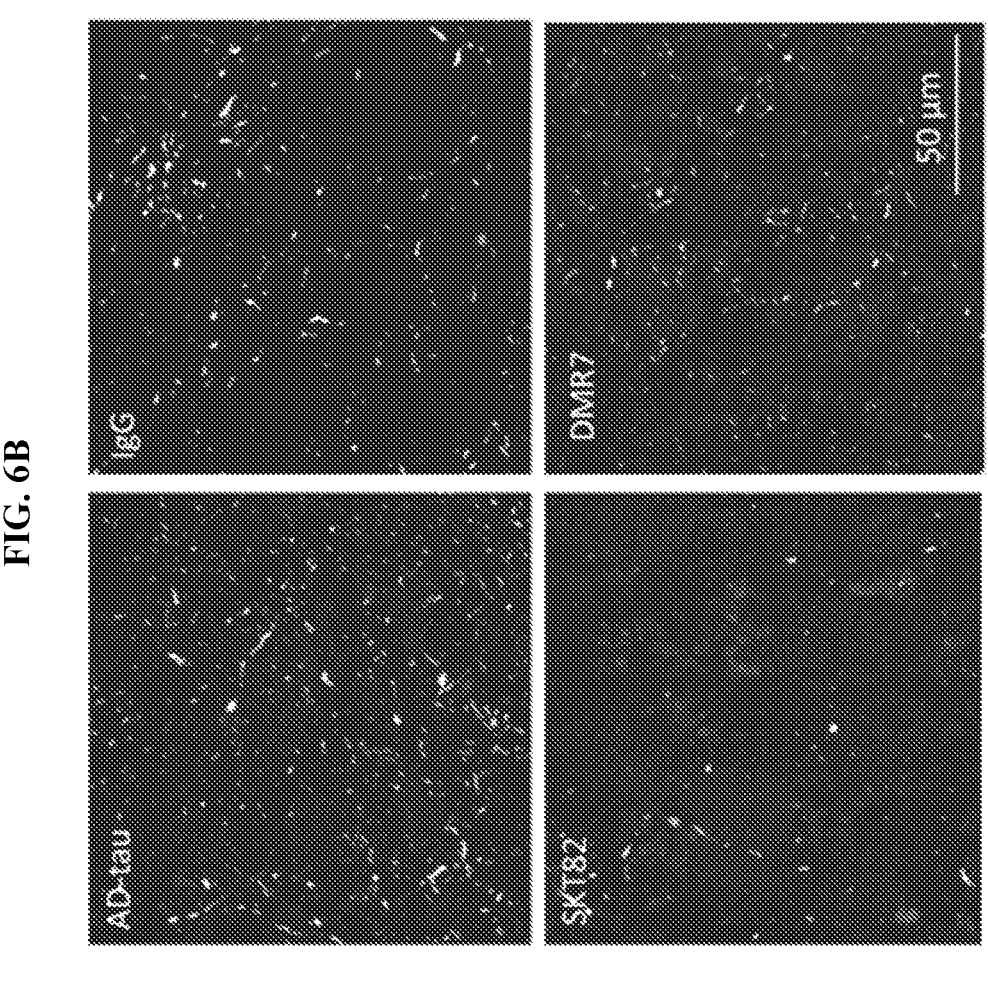
FIGS. 6A-6B: Tau mAbs inhibit seeded aggregation of tau pathology in slice cultures.
Figure 6A:
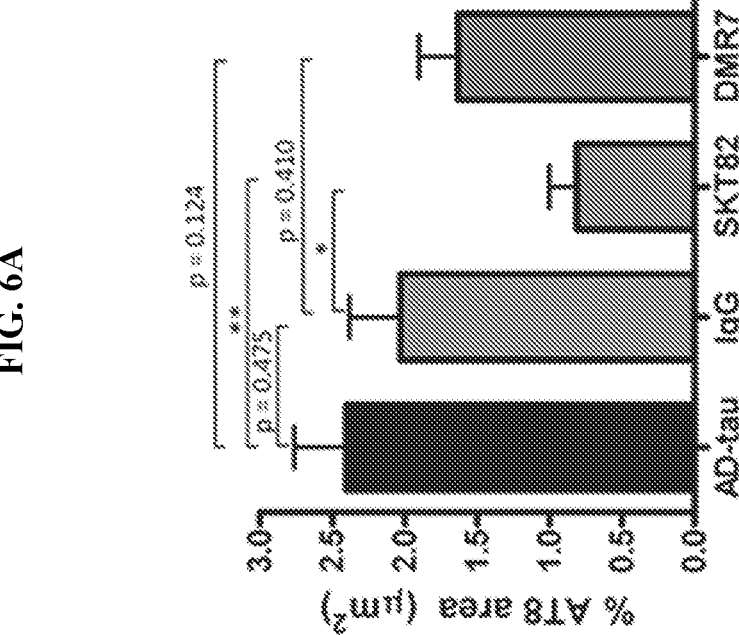

To expand on the primary neuron studies of AD-tau induced pathology, hippocampal slice cultures from WT mice were co-treated with the tau mAbs and AD-tau. Similar to what is observed with primary neurons. AD-tau treatment of hippocampal slice cultures results in recruitment of endogenous mouse tau into insoluble tau aggregates that are detected with the phospho-tau antibody. AT8. The seeding of AT8-positive tau inclusions by AD-tau is significantly inhibited by SKT82 and there is a trend towards reduction of pathology by DMR7 that did not achieve statistical significance (FIGS. 6A-6B). These studies further confirm that the conformation-selective tau mAbs can inhibit AD-tau seeding of mouse tau pathology in neurons, here utilizing a more complex culture system.

Example 7: DMR7 and SKT82 Inhibit Pathological Tau Transmission In Vivo

Given the selective binding of DMR7 and SKT82 to pathological tau, as well as inhibition of AD-tau seeded aggregation in primary neurons and cortical slice cultures, it was evaluated whether these tau mAbs inhibit the transmission of tau pathology in vivo. Intracerebral injection of AD-tau into the 5×FAD mouse model of Aβ plaque formation induces NP tau pathology in dystrophic neurites surrounding AB plaques, recapitulating the hallmark plaque and tau pathology observed in AD brain. In addition, seeded aggregation of tau in 5×FAD mice does not rely on transgenic overexpression of mutant human tau to develop tau pathology, as AD-tau induces fibrillization of endogenous mouse tau that accumulates in plaque-associated neuronal processes. A prevention model of antibody treatment was employed in which 4 month old 5×FAD female mice received i.p. injections of 60 mg/kg of SKT82, DMR7, or isotype-matched IgG controls four days prior to unilateral injection of AD-tau into the hippocampus. Mice subsequently received the same mAb doses on the day of AD-tau injection and weekly thereafter for 3 months. To confirm CNS exposure to the mAbs, the levels of SKT82 and DMR7 were assessed in the CSF and plasma of mice 4 and 7 days post-injection, with nanomolar (nM) levels of antibody detected in CSF and μM levels found in plasma, providing a CSF/Plasma ratio from 0.12-0.31% (Table 1) that is consistent with previously published ratios of IgG molecules.

AD-tau induced pathology in the treated 5×FAD mice was evaluated by IHC and biochemical extraction of soluble and insoluble tau to assess total tau and phospho-tau levels. Both SKT82 and DMR7 significantly inhibited tau pathology in the contralateral hippocampus (FIG. 7A), a region distant from the site of initial AD tau seeding. Quantification of AT8-positive pathological tau area in the contralateral hippocampus revealed a statistically significant reduction of 32.8% with SKT82 treatment and a 31.7% decrease after DMR7 dosing (FIG. 7B). Moreover. SKT82 significantly reduced ipsilateral AT8 pathology area by 27.0%, although DMR7 did not influence the ipsilateral tau pathology, consistent with SKT82 exhibiting greater efficacy in the slice culture model.

Figures 8A, 8B:
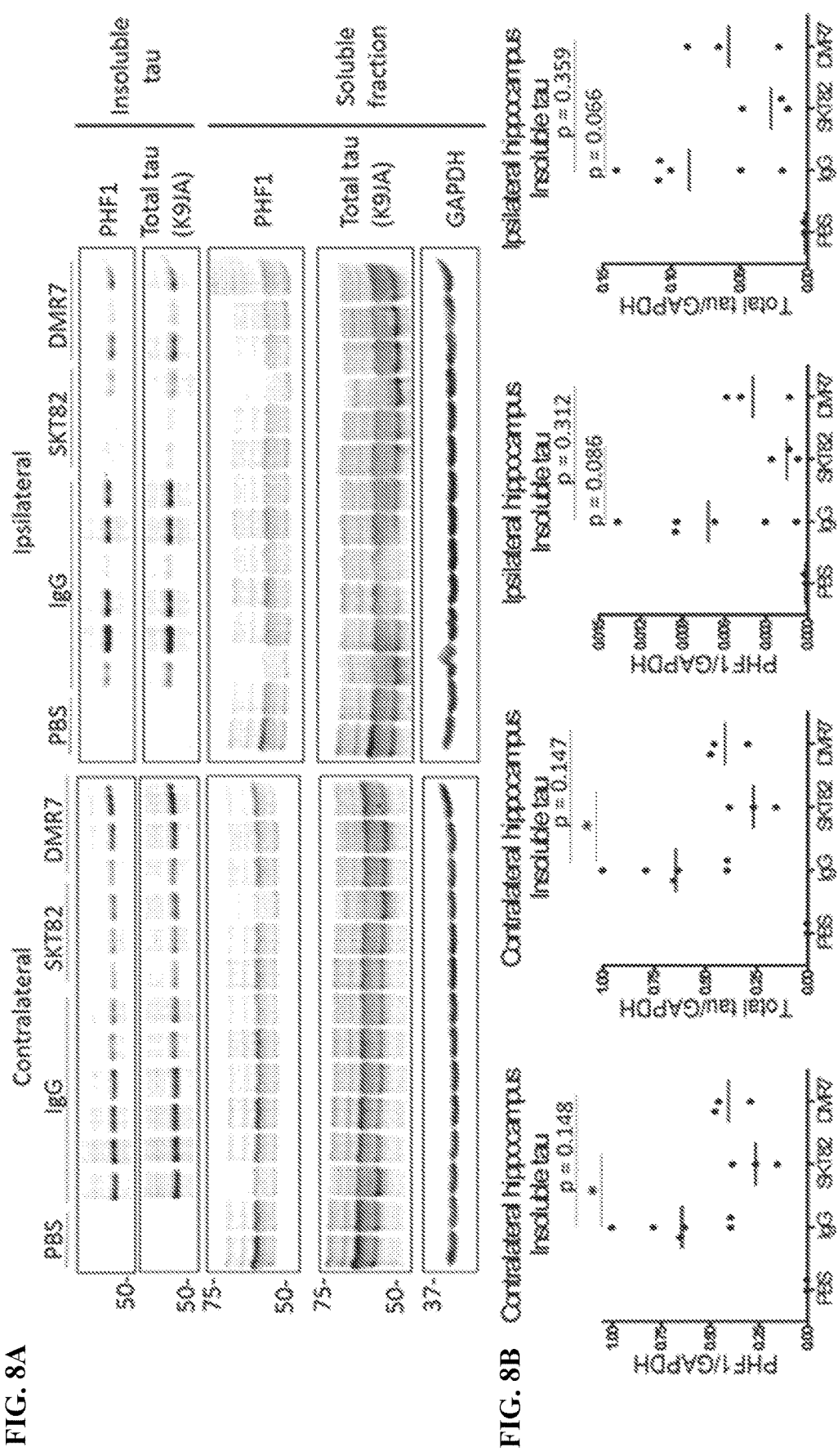
FIGS. 8A-8B: DMR7 and SKT82 inhibit insoluble tau aggregates.
Figure 10:
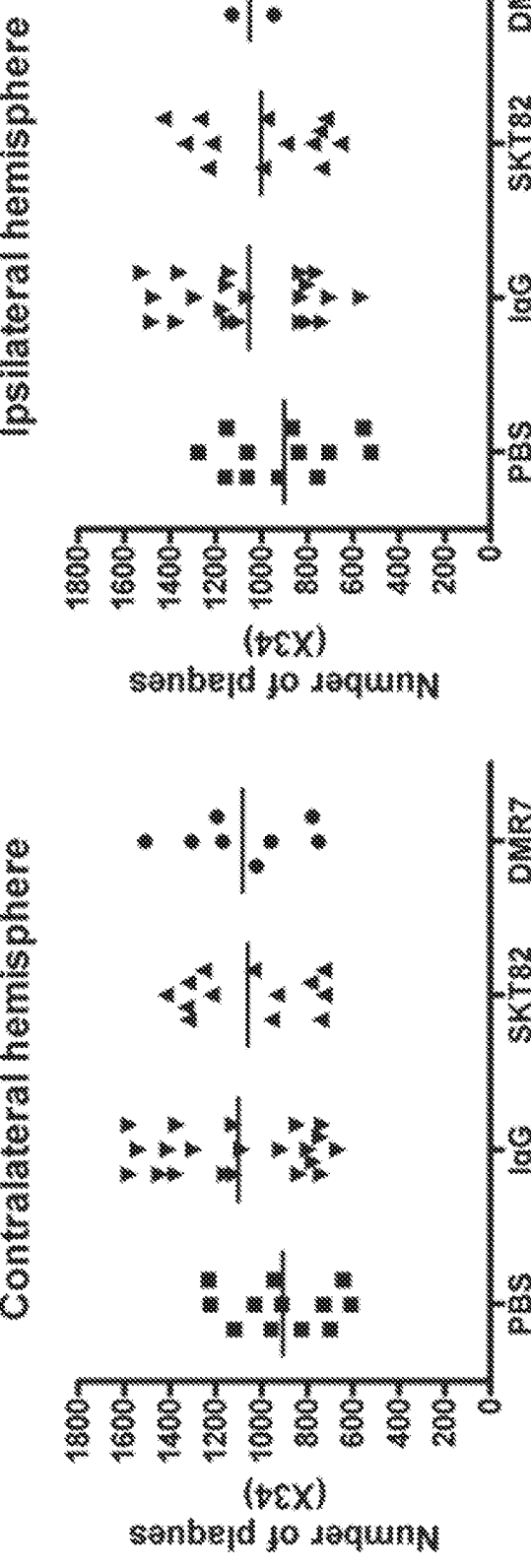
FIG. 10: Tau mAbs do not influence amyloid-beta (AB) plaque burden in 5×FAD mice. X34 staining of Aβ plaques revealed no differences between PBS- and AD-tau-injected mice. Furthermore, tau mAb treatment compared to IgG controls did not alter the AB plaque load indicating that the reduction in tau pathology is not a result of altered AB levels. No statistically significant differences based on one-way ANOVA with Tukey's post-hoc analysis.
Figure 11:
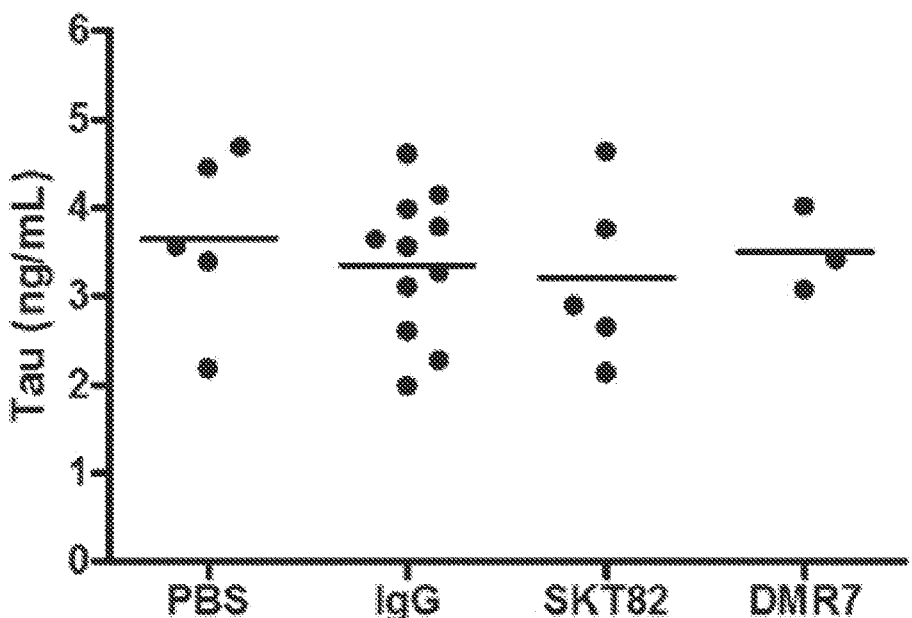
FIG. 11: Pharmacokinetics of tau mAb blood-brain barrier penetrance and CSF tau levels. Electrochemiluminescence assay of endogenous mouse tau levels in CSF of 5×FAD mice revealed no changes in total tau levels following AD-tau injection and 3 months tau mAb treatments. See also Table 1: ELISA assays of DMR7 and SKT82 levels in CSF and plasma at 4 and 7 days post treatment demonstrate relative CSF to plasma ratios of 0.22-0.31% for DMR7 and 0.12-0.14% for SKT82 consistent with previous reports of IP administered IgG immunotherapies.
Figure 12:
FIG. 12: Schematic of tau monoclonal antibody (mAb) in vivo treatment of 5×FAD mice. 4 month old 5×FAD mice were treated by intraperitoneal (IP) injection with 60 mg/kg tau mAbs or IgG control 4 days prior and on the day of intracranial injection of Alzheimer's brain derived tau (AD-tau). AD-tau was stereotaxically injected unilaterally into the hippocampus and were treated with weekly IP injections of tau mAbs or IgG control for 3 months. Control mice were injected with PBS in the hippocampus and did not receive antibody treatment.

To demonstrate that AT8 positive tau pathology detected by IHC represents insoluble pathological tau aggregates, sequential biochemical extractions of ipsilateral and contralateral hippocampi were performed to examine insoluble and soluble tau levels by immunoblot, probing with the PHF1 antibody that recognizes pathological tau that is phosphorylated at Ser396/Ser404. SKT82 and DMR7 treatment led to lower insoluble phosphorylated tau and total tau in the ipsilateral and contralateral sides of AD-tau injected 5×FAD mice (FIGS. 8A-8B), with these decreases being significant for SKT82 in the contralateral hippocampus (58.4% and 58.5% reduction of PHF1 and total tau, respectively). Although SKT82 treatment resulted in a 78.8% reduction of phospho-tau and 69.1% reduction of total tau in the ipsilateral hippocampus, this did not achieve statistical significance due to variability within the IgG control group. Similarly. DMR7 treatment led to reductions of phosphorylated tau and total tau on both the ipsilateral and the contralateral sides that also did not achieve statistical significance due to the variability of the IgG group, perhaps highlighting an inherent limitation of the model system requiring AD-tau injection. To ensure that the observed variability was not due to variations in the number of Aβ plaques and tau-enriched plaque-associated dystrophic processes, the plaque burden was evaluated in mice using the amyloid-plaque binding dye X-34 and did not detect changes between groups (FIG. 10). Taken together, these results demonstrate that nM concentrations of SKT82 and DMR7 are able to penetrate the blood-brain barrier, thereby inhibiting the development of tau pathology in AD-tau seeded 5×FAD mice exhibiting neuropathological hallmarks of AD.

Example 8: AD-Tau Pathology in 5×FAD Mice Did not Influence Behavior of 7-Month Old Mice To assess the behavioral phenotypes of 7-month old 5×FAD mice treated for 11-13 weeks with SKT82 and

TABLE 1

Pharmacokinetics of tau mAb blood-brain barrier penetrance. ELISA assays of DMR7 and SKT82 levels in CSF and plasma of mice 4- and 7-days post-IP injection quantified in comparison to standard curves of purified DMR7 and SKT82.

| | Dose (mg/kg) | Days post injection | Plasma (μM) | Plasma % CV | CSF (nM) | CSF % CV | CSF/plasma ratio (%) |
|---|---|---|---|---|---|---|---|
| DMR7 n = 3 | 60 | 4 | 1.29 ± 0.22 | 17 | 3.78 ± 0.95 | 25 | 0.31 ± 0.12 |
| DMR7 n = 3 | 60 | 7 | 1.24 ± 0.45 | 36 | 2.9 ± 1.9 | 66 | 0.22 ± 0.08 |
| SKT82 n = 2 | 60 | 4 | 0.91 ± 0.24 | 26 | 1.20 ± 0.06 | 5 | 0.14 ± 0.03 |
| SKT82 n = 3 | 60 | 7 | 0.65 ± 0.19 | 30 | 0.70 ± 0.16 | 28 | 0.12 ± 0.06 |

Figures 9A, 9B, 9C:
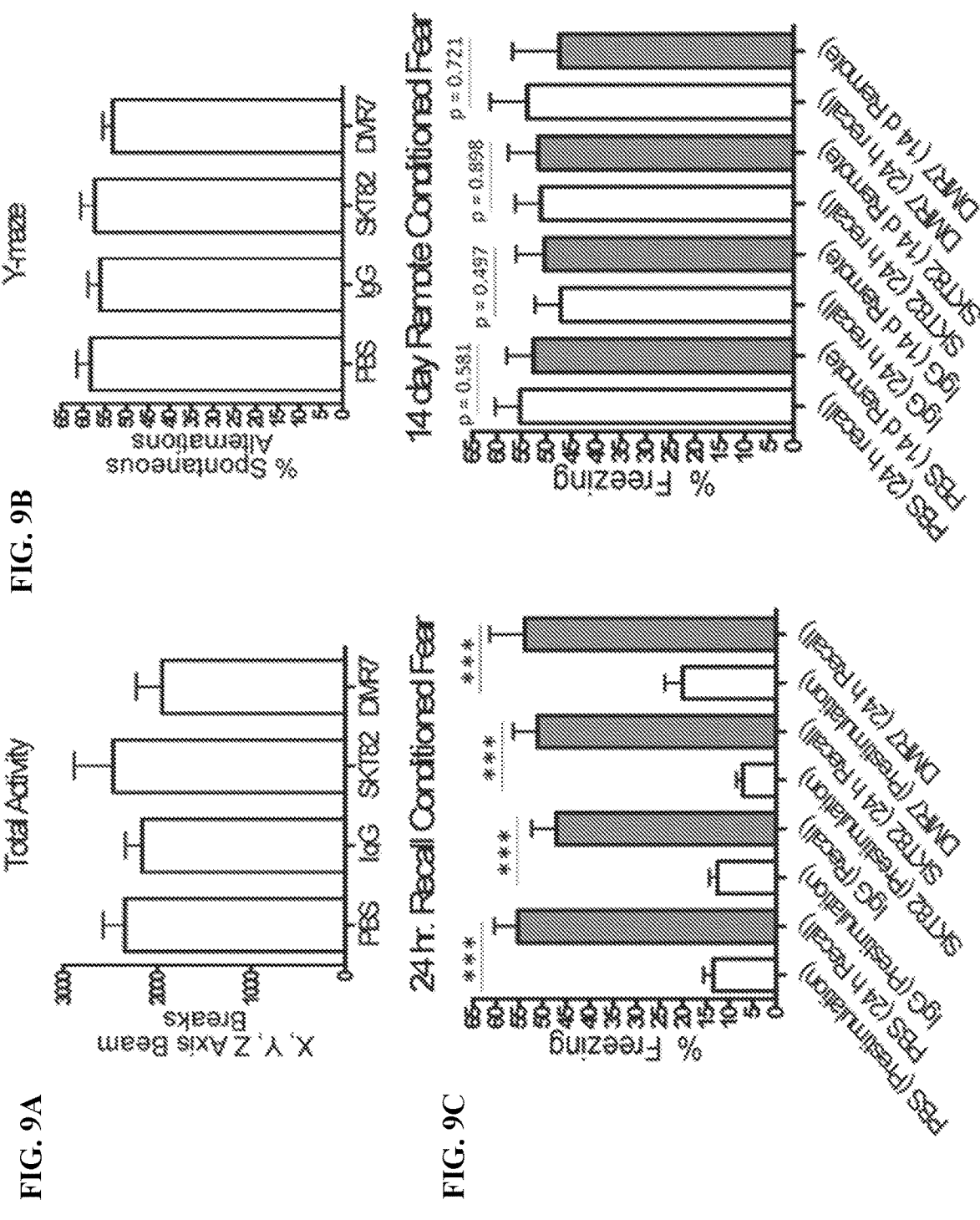
FIGS. 9A-9C: Behavioral characterization of 7-month old 5×FAD mice 3 month post-AD-tau injection.

DMR7 after AD-tau injection, open-field, Y-maze, and contextual fear conditioning tests were performed. SKT82 and DMR7 were generally well tolerated and did not influence total motor activity of mice in the open field test (FIG. 9A). Similarly, no changes were observed in Y-maze spontaneous alternations between PBS-injected mice without tau pathology and AD-tau-injected mice having significant tau pathology that were treated with IgG controls or either tau antibody (FIG. 9B). The contextual fear conditioning 24-hour recall test demonstrated increased freezing behavior compared to that observed during training, demonstrating that all groups learned the contextual cues to anticipate foot shock (FIG. 9C). Upon remote recall testing 2 weeks after initial training, no deficits in control IgG-treated AD-tau-injected 5×FAD mice with tau pathology were observed as compared to the PBS group lacking tau pathology. Thus, behavioral deficits were not detectable in the 5×FAD mice 3-months after AD-tau injection using these tests. Although this prevented assessment of whether SKT82 or DMR7 may provide cognitive benefits in this model system, the tau mAb treatments were well tolerated and did not independently elicit any behavioral deficits.

Here, two novel tau mAbs that bind selectively to the pathological misfolded conformation of tau compared to tau monomer are disclosed, with discontinuous epitopes in the proline-rich central domain of tau and the C-terminal domain that are detectable in multiple human tauopathies. Binding of SKT82 and DMR7 to tau seeds prevents their uptake into primary neurons and inhibits the seeded aggregation of tau in WT mouse primary neurons and hippocampal slice cultures. Utilizing 5×FAD mice that harbor Aβ plaques, human brain-derived AD-tau injection induces robust endogenous mouse tau pathology that 20) is inhibited by both SKT82 and DMR7, with SKT82 causing a reduction of both ipsilateral and contralateral tau pathology as assessed by IHC and biochemical extraction of insoluble tau from treated mice.

In certain embodiments, SKT82 and DMR7 were developed against human AD brain-derived insoluble tau extracts, and thus are able to detect pathological tau species present in human disease. As shown herein. DMR7 and SKT82 were evaluated in the context of physiological endogenous mouse tau with AD-tau seeded pathology.

DMR7 and SKT82 have similar binding affinities, selectivity, and epitopes, and yet SKT82 was more effective than DMR7 at inhibiting tau pathology in slice cultures and the ipsilateral hippocampus in vivo. Without wishing to be limited by any theory, one possible explanation is that AD-tau bound by SKT82 may be cleared more actively since SKT82 is a mouse IgG2a isotype that activates microglial FC receptors, whereas DMR7 is mouse IgG1 that does not induce a microglial response in murine models.

The present results demonstrate that DMR7 and SKT82 inhibit seeded aggregation of tau pathology in primary neurons by blocking the uptake of fluorescently-labeled tau seeds. In certain non-limiting embodiments, the epitopes of tau bound by mAbs may influence the ability of mAb to block neuronal uptake of tau.

The present studies did not demonstrate significant changes in the Aβ plaque burden upon induction of tau pathology with AD-tau injection or changes upon reduction of tau pathology with SKT82 or DMR7. In certain non-limiting embodiments, this may be caused by the relatively aggressive plaque deposition in 5×FAD mice relative to other mouse models. The study did not show changes in freezing during remote recall of contextual fear conditioning, which in certain embodiments may be due to young mice used in the present study or chronic handling of mice for weekly i.p. injections of mAbs.

Given the great demand for tau immunotherapy candidates, it is crucial to explore tau mAbs with varying affinities, epitopes, and isotypes. The present disclosure provides two novel candidates with unique conformational epitopes that selectively bind AD-tau compared to tau monomer. SKT82 and DMR7 reduce tau pathology in vitro and in an AD model with multiple neuropathological hallmarks of AD.

Enumerated Embodiments

The recitation of a listing of elements in any definition of a variable herein includes definitions of that variable as any single element or combination (or sub-combination) of listed elements. The recitation of an embodiment herein includes that embodiment as any single embodiment or in combination with any other embodiments or portions thereof.

The following enumerated embodiments are provided, the number of which is not to be construed as designating levels of importance.

Embodiment 1 provides an isolated monoclonal antibody comprising a light chain variable region (VL) and a heavy chain variable region (VH), wherein the VL comprises a CDR1 region comprising the amino acid sequence of SEQ ID NOs: 23 or 51: a CDR2 region comprising the amino acid sequence of SEQ ID NOs: 25 or 53; and a CDR3 region comprising the amino acid sequence of SEQ ID NOs: 27 or 55, and wherein the VH comprises a CDR1 region comprising the amino acid sequence of SEQ ID NOs: 9 or 37: a CDR2 region comprising the amino acid sequence of SEQ ID NOs: 11 or 39; and a CDR3 region comprising the amino acid sequence of SEQ ID NOs: 13 or 41.

Embodiment 2 provides the monoclonal antibody of Embodiment 1, wherein the VL comprises a CDR1 region comprising the amino acid sequence of SEQ ID NO: 23: a CDR2 region comprising the amino acid sequence of SEQ ID NO: 25; and a CDR3 region comprising the amino acid sequence of SEQ ID NO: 27; and wherein the VH comprises a CDR1 region comprising the amino acid sequence of SEQ ID NO: 9; a CDR2 region comprising the amino acid sequence of SEQ ID NO: 11; and a CDR3 region comprising the amino acid sequence of SEQ ID NO: 13.

Embodiment 3 provides the monoclonal antibody of Embodiment 1, wherein the VL comprises a CDR1 region comprising the amino acid sequence of SEQ ID NO: 51: a CDR2 region comprising the amino acid sequence of SEQ ID NO: 53; and a CDR3 region comprising the amino acid sequence of SEQ ID NO: 55, and wherein the VH comprises a CDR1 region comprising the amino acid sequence of SEQ ID NO: 37: a CDR2 region comprising the amino acid sequence of SEQ ID NO: 39; and a CDR3 region comprising the amino acid sequence of SEQ ID NO: 41.

Embodiment 4 provides the monoclonal antibody of any one of Embodiments 1-3, wherein the VL comprises the amino acid sequence of SEQ ID NOs: 60 or 64, and wherein the VH comprises the amino acid sequence of SEQ ID NOs: 58 or 62.

Embodiment 5 provides the monoclonal antibody of any one of Embodiments 1-4, wherein: (a) the VL comprises the amino acid sequence of SEQ ID NO: 60, and the VH comprises SEQ ID NO: 58; and (b) the VL comprises the amino acid sequence of SEQ ID NO: 64, and the VH comprises SEQ ID NO: 62.

Embodiment 6 provides the monoclonal antibody of any one of Embodiments 1-5, which is humanized.

Embodiment 7 provides the monoclonal antibody of any one of Embodiments 1-6, which is labeled.

Embodiment 8 provides a pharmaceutical composition comprising the monoclonal antibody of any one of Embodiments 1-7 and at least one pharmaceutical excipient.

Embodiment 9 provides an isolated polynucleotide comprising at least one of the nucleic acid sequences of SEQ ID NOs: 57, 59, 61, or 63.

Embodiment 10 provides the polynucleotide of Embodiment 9, comprising: (a) the nucleic acid sequences of SEQ ID NOs: 57 and 59; or (b) the nucleic acid sequences of SEQ ID NOs: 61 and 63.

Embodiment 11 provides a method of preventing, minimizing, and/or reversing fibrillization of native tau, the method comprising contacting the native tau with an effective amount of the isolated monoclonal antibody of any one of Embodiments 1-7.

Embodiment 12 provides a method of preventing or minimizing transmission of pathological tau to a cell and/or uptake of pathological tau by a cell, the method comprising contacting the cell with an effective amount of the isolated monoclonal antibody of any one of Embodiments 1-7.

Embodiment 13 provides the method of Embodiment 11, wherein the native tau is within a cell.

Embodiment 14 provides the method of any one of Embodiments 12-13, wherein the cell is in vivo.

Embodiment 15 provides the method of any one of Embodiments 12-14, wherein the cell comprises a neuron.

Embodiment 16 provides a method of reducing and/or preventing further increase in any intraneuronal tau aggregates or inclusions in a subject, the method comprising administering to the subject a therapeutically effective amount of the isolated monoclonal antibody of any one of Embodiments 1-7.

Embodiment 17 provides a method of treating, preventing, and/or ameliorating a tauopathy in a subject, the method comprising administering to the subject a therapeutically effective amount of the isolated monoclonal antibody of any one of Embodiments 1-7.

Embodiment 18 provides the method of Embodiment 17, wherein the tauopathy comprises Alzheimer's Disease, Pick's disease, Corticobasal degeneration, Argyrophilic grain disease (AGD), Primary age-related tauopathy (PART)/Neurofibrillary tangle-predominant senile dementia, Chronic traumatic encephalopathy (CTE), Progressive supranuclear palsy (PSP), Corticobasal degeneration (CBD), Frontotemporal dementia and parkinsonism linked to chromosome 17 (FTDP-17), Lytico-bodig disease (Parkinson-dementia complex of Guam), Ganglioglioma and gangliocytoma, Meningioangiomatosis, Postencephalitic parkinsonism, Subacute sclerosing panencephalitis (SSPE), Lead encephalopathy, Tuberous sclerosis, Pantothenate kinase-associated neurodegeneration, and/or Lipofuscinosis.

Embodiment 19 provides the method of any one of Embodiments 17-18, wherein the administering reduces or prevents further increase in any intraneuronal tau aggregates or inclusions in the subject.

Embodiment 20 provides the method of any one of Embodiments 16-19, wherein the antibody is provided to the subject as a pharmaceutical composition.

Embodiment 21 provides the method of any one of Embodiments 16-20, wherein the antibody is administered parenterally to the subject.

Embodiment 22 provides a method of detecting a tauopathy in a subject, the method comprising administering to the subject a labeled isolated monoclonal antibody of any one of Embodiments 1-7, and detecting presence or absence of a complex of the labeled isolated monoclonal antibody with any pathological tau present in the subject, wherein, if the complex is detected, the subject has a tauopathy.

Embodiment 23 provides a method of detecting pathological tau in a sample, the method comprising contacting the sample with a labeled isolated monoclonal antibody of any one of Embodiments 1-7, and detecting presence or absence of a complex of the labeled isolated monoclonal antibody with any pathological tau present in the sample, wherein, if the complex is detected, pathological tau are present in the sample.

Embodiment 24 provides an isolated monoclonal antibody, or fragment thereof, which recognizes a conformational epitope comprising amino acids 151-244 and amino acids 369-441 of pathological tau, and which affinity for pathological tau is higher than for native tau.

Embodiment 25 provides the isolated monoclonal antibody of Embodiment 24, which further recognizes amino acids 120-151 of pathological tau.

Embodiment 26 provides an autonomously replicating or an integrative mammalian cell vector comprising a recombinant nucleic acid encoding an antibody comprising a light chain variable region (VL) and a heavy chain variable region (VH), wherein the VL comprises a CDR1 region comprising the amino acid sequence of SEQ ID NOs: 23 or 51: a CDR2 region comprising the amino acid sequence of SEQ ID NOs: 25 or 53; and a CDR3 region comprising the amino acid sequence of SEQ ID NOs: 27 or 55, and wherein the VH comprises a CDR1 region comprising the amino acid sequence of SEQ ID NOs: 9 or 37; a CDR2 region comprising the amino acid sequence of SEQ ID NOs: 11 or 39; and a CDR3 region comprising the amino acid sequence of SEQ ID NOs: 13 or 41.

Embodiment 27 provides the vector of Embodiment 26, which comprises a plasmid or a virus.

Embodiment 28 provides the vector of any one of Embodiments 26-27, which comprises a mammalian cell expression vector.

Embodiment 29 provides the vector of any one of Embodiments 26-28, further comprising at least one nucleic acid sequence that directs and/or controls expression of the antibody.

Embodiment 30 provides an isolated host cell comprising the vector of any one of Embodiments 26-29.

Embodiment 31 provides the cell of Embodiment 30, which is a non-human cell.

Embodiment 32 provides the cell of any one of Embodiments 30-31, which is mammalian.

The disclosures of each and every patent, patent application, and publication cited herein are hereby incorporated herein by reference in their entirety.

While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. An isolated monoclonal antibody comprising a light chain variable region (VL) and a heavy chain variable region (VH), wherein:

(a) the VL comprises
  a Complementarity-Determining Region 1 (CDR1) region comprising the amino acid sequence of SEQ ID NO: 23;
  a Complementarity-Determining Region 2 (CDR2) region comprising the amino acid sequence of SEQ ID NO: 25; and
  a Complementarity-Determining Region 3 (CDR3) region comprising the amino acid sequence of SEQ ID NO: 27, and
the VH comprises
  a CDR1 region comprising the amino acid sequence of SEQ ID NO: 9;
  a CDR2 region comprising the amino acid sequence of SEQ ID NO: 11; and
  a CDR3 region comprising the amino acid sequence of SEQ ID NO: 13, or
(b) the VL comprises
  a CDR1 region comprising the amino acid sequence of SEQ ID NO: 51;
  a CDR2 region comprising the amino acid sequence of SEQ ID NO: 53; and
  a CDR3 region comprising the amino acid sequence of SEQ ID NO: 55, and
the VH comprises
  a CDR1 region comprising the amino acid sequence of SEQ ID NO: 37;
  a CDR2 region comprising the amino acid sequence of SEQ ID NO: 39; and
  a CDR3 region comprising the amino acid sequence of SEQ ID NO: 41.

2. The monoclonal antibody of claim 1, wherein:

(a) the VL comprises the amino acid sequence of SEQ ID NO: 60, and the VH comprises SEQ ID NO: 58; or (b) the VL comprises the amino acid sequence of SEQ ID NO: 64, and the VH comprises SEQ ID NO: 62.

3. The monoclonal antibody of claim 1, which is humanized.

4. The monoclonal antibody of claim 1, which is labeled.

5. A pharmaceutical composition comprising the monoclonal antibody of claim 1 and at least one pharmaceutical excipient.

6. An isolated nucleic acid molecule comprising polynucleotides encoding the monoclonal antibody (a) or (b) of claim 1.

7. The nucleic acid molecule of claim 6, wherein the polynucleotides encoding the monoclonal antibody (a) comprise the nucleic acid sequences of SEQ ID NOs: 57 and 59; and the polynucleotides encoding the monoclonal antibody (b) comprise (b) the nucleic acid sequences of SEQ ID NOs: 61 and 63.

8. An expression vector comprising a recombinant nucleic acid encoding the monoclonal antibody of claim 1.

9. The expression vector of claim 8, wherein the expression vector is (a) a plasmid or a virus vector; or (b) a mammalian cell expression vector.

10. An isolated host cell comprising the vector of claim 8, optionally wherein the host cell is a non-human cell or a mammalian cell.

11. A method of detecting pathological tau in a sample isolated from a subject, the method comprising contacting the sample with a labeled isolated monoclonal antibody of claim 1, and detecting presence or absence of a complex of the labeled isolated monoclonal antibody with any pathological tau present in the sample, wherein the pathological tau comprises a misfolded tau comprising amino acids 151-244 and amino acids 369-441 of Tau-F (SEQ ID NO:69); and wherein the presence of the complex of the labeled isolated monoclonal antibody with the pathological tau indicates that the subject has tauopathy.

* * * * *